United States Patent [19]

Baird et al.

[11] Patent Number: 5,120,861

[45] Date of Patent: Jun. 9, 1992

[54] DIAZIRINE DERIVATIVES OF AROMATIC HETEROCYCLIC COMPOUNDS

[75] Inventors: Mark S. Baird, Newcastle-upon-Tyne; Ian Bruce, Oxford, both of United Kingdom

[73] Assignee: Shell Research Limited, United Kingdom

[21] Appl. No.: 614,447

[22] Filed: Nov. 16, 1990

[30] Foreign Application Priority Data

Nov. 16, 1989 [GB] United Kingdom ............... 8925977

[51] Int. Cl.$^5$ .......................................... C07D 405/04
[52] U.S. Cl. ................................. 548/960; 546/276; 548/202; 548/214; 548/235; 548/247
[58] Field of Search .................. 546/276; 549/59, 472; 548/960

[56] References Cited

U.S. PATENT DOCUMENTS 3,637,663  1/1972  Mitsch ................................. 548/960

OTHER PUBLICATIONS

Chemical Abstracts, vol. 93, No. 11, Abstract No.: 113490y, Sep. 1980.

Chemical Abstracts, vol. 113, No. 1, Abstract No.: 6110j, Jul. 1990.

Chemical Abstracts, vol. 113, No. 5, Abstract No.: 40367h, Jul. 1990.

Chemical Abstracts, vol. 113, No. 9, Abstract No.: 78053r, Aug. 1990.

Primary Examiner—Mary C. Lee
Assistant Examiner—Jacqueline Haley

[57] ABSTRACT

Compounds of the formula

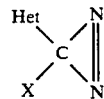

I in which Het represents an optionally substituted aromatic heterocycle having a sulphur or oxygen hetero atom and attached via a ring carbon atom, and X is halogen, alkyl, alkaryl, cyano, alkoxy, mono- or di-alkylamino, acyloxy or aryl, are useful intermediates to a range of cyclopropane derivatives. Processes for their preparation and their use in further synthetic processes are also described.

6 Claims, No Drawings

DIAZIRINE DERIVATIVES OF AROMATIC HETEROCYCLIC COMPOUNDS

The present invention relates to diazirine derivatives of aromatic heterocyclic compounds, more usually halodiazirine derivatives of such compounds, processes for producing such compounds and processes in which the compounds are reacted in thermolytic or photolytic reaction in the presence of an olefinic compound and novel cyclopropane derivatives produced in that process.

I. E. Dolgii, K. N. Shavrin and I. V. Krylova, in Izv. Akad. Nauk. USSR, Ser. Khim., 11, (1984) 2644 report the reaction of 2-dichloromethylthiophene and the corresponding 2-furyl derivative with potassium t-butoxide in the presence of 18-crown-6 and 2-methylpropene as well as propene, cis- and trans-but-2-ene, 2,3-dimethylbut-2-ene and 2-methylbut-2-ene. K. I. Rubina, Yu. Sh. Gol'dberg and M. V. Shimanskaya in Khim. Geterotskl. Soedin. (1985) 8 1138-1139 describe a similar reaction in which 2- and 3-dichloromethyl pyridine are reacted with 2,3-dimethylbut-2-ene in the presence of potassium t-butoxide to form 2- and 3-(2,2,3,3-tetramethyl-1chlorocyclo propyl)pyridine. However the dihalomethyl derivatives are somewhat unstable and the yields from the cyclopropanations have been found to be variable and product purification sometimes to be difficult.

Saito et al. in Bull. Chem. Soc. Japan 60 (1987) 4317 describe the production of 2- and 3-thienylmethylene carbenes with olefinic compounds. The carbenes were produced in situ from the corresponding carbaldehyde tosylhydrazone.

Gronowitz and Liljefors in Acta Chem. Scand. 831 (1977) 771-780, describe the formation of 2- and 3-thienylamidine hydrochlorides which are subsequently reacted with 3-(dimethylamino)-propenal to form pyrimidines.

Graham in J. Am. Chem. Soc. 87 (1965) 4396-7 described the formation of a range of aryl, alkyl and alkenyl 3-halo-diazirines from the corresponding amidine reaction with sodium hypohalite in dimethylsulphoxide in the presence of water, saturated sodium chloride and lithium chloride. He also described their thermolytic decomposition to form carbenes which could be captured by alkenes to form cyclopropanes, e.g., cyclohexene to form a norcararane compound.

H. Berneth and S. Huenig in Chem. Ber. (1980) 113 2040-2042 describe the production of 4-pyridyl and phenyl 3-chloro diazirines.

In "Chemistry of Diazirines" ed MTHLiu (Vol I) Schmitz reviews methods of forming diazirines. The formation of a range of alkyl, alkenyl, alkoxy, aralkyl, aryl and aryloxy halodiazirines from the corresponding amidines is described. The use of diazirines as carbene sources inter alia for reaction with alkenes, is reviewed in Vol II by Doyle and by Liu.

In the invention there is provided a new compound of the formula I

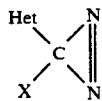

in which Het represents an optionally substituted aromatic heterocycle having a sulphur or oxygen hetero atom attached via a ring carbon atom and X is hydrogen, halogen, alkyl, aralkyl, cyano, alkoxy, mono- or di-alkyl amino, acyloxy or aryl, in which any of the alkyl or aryl groups may be unsubstituted or substituted.

In the compound a heterocycle Het may be unsubstituted or substituted on one or more of the ring carbon atoms or on a ring hetero atom. Substituents are for instance halogen atoms, alkyl, cycloalkyl, aryl, aralkyl, alkaryl, alkoxy or aryloxy, in which any of the alkyl or aryl groups may be substituted or unsubstituted. The heterocycle may be a 5- or 6-membered ring and may bear 1 or more fused rings. The ring may contain two or more hetero atoms but preferably contains a single hetero atom. Although the hetero atom may be nitrogen alone in which case it is preferably a 6-membered ring (pyridine derivative), it preferably includes oxygen, or most preferably, sulphur and, in either case, optionally also nitrogen in which case it is preferably a 5-membered ring. The preferred compounds are thus furyl derivatives, thienyl derivatives or thiazyl derivatives. The heterocyclic ring is usually attached to the carbon atom in formula I via the 2- or 3- carbon atom.

In the new compound X preferably represents a halogen atom, usually selected from chlorine and bromine, most preferably chlorine.

In another aspect of the invention there is provided a process for producing the novel diazirine compounds of the formula I above in which X is halogen (usually chlorine or bromine), in which the corresponding amidine is halogenated in the presence of water and a water miscible organic solvent. The solvent is a polar aprotic solvent and may be, for instance, dimethyl formamide, HMPA or Sulpholane. Most preferably the reaction is carried out in aqueous dimethyl sulphoxide (DMSO) solution. The halogenation is conducted by the addition of sodium hypohalite, usually in the presence of additional sodium halide, and optionally also in the presence of lithium halide. The halogen atom which becomes substituted on the carbon atom of the diazirine compound is derived from the hypohalite, which is thus preferably selected from the hypobromite or, preferably the hypochlorite.

The process is carried out under conditions of temperature and time to maximise production of the diazirine whilst minimising side reactions. The temperature should thus be sufficiently high to avoid formation of the N-haloamidine, but should not be so high as to lead to decomposition of the diazirine which results in the formation of the aldehyde by trapping of the carbene by water. The optimum temperature varies depending on the starting amidine but in general lies in the range 25°-60° C. For 2-thienylamidine hydrochloride the optimum temperature is in the range 30°-40° C., for a period of around 5-30 minutes. For the 3-thienylamidine hydrochloride the optimum temperature is in the range 40°-50° C. for a period in the range 5-30 minutes.

The halodiazirine is recovered and purified using conventional techniques. The pure product is preferably diluted with a non-polar solvent for storage in order to minimize azine formation, as discussed above.

The halogen (usually chlorine or bromine) substituted diazirines produced in the process may be further reacted by exchange of the halogen for other groups, to produce other novel diazirines in which X is other than halogen for instance by reactions analogous to those described by R. A. Moss in Chemistry of Diazirines (op cit) vol 1 chapter IV, to produce the corresponding compounds in which X is cyano, fluoro, acyloxy, alkoxy, NH alkyl and N(alkyl)₂.

The amidine compound is generally used in the form of its hydrochloride. Such compounds are known, and are produced generally from the corresponding cyano derivative, for instance as described in Acta Chem. Scand. B 31 771–780 (1977) by Gronowitz et al.

The novel compounds are useful as starting materials for the thermolytic or photolytic production of carbenes and the subsequent trapping of carbenes, for instance by compounds having an ethylenic bond to produce cyclopropane derivatives. Cyclopropanes show a wide range of biological activities and are useful as for instance fungicides and miticides, e.g. the pyrethroid-type compounds, as well as a range of interesting pharmaceutical activities, for instance adenosive derivatives can have anti-psychotic properties as described in EP-A-0232813 and tertiary amine group containing compounds of GB-A-2192631 can have fungicidal properties. Furthermore the cyclopropanes could be used as intermediates to be used in the synthesis of a large number of other compounds which have useful activities resulting from the presence of the aromatic heterocyclic group and/or other groups which could subsequently be introduced. For instance the halogen substituted cyclopropanes could be dehydrohalogenated to lead to cyclopropenes which could subsequently be used in cycloaddition reactions to produce further heterocyclic compounds. Also the cyclopropanes could be subjected to ring opening reactions to produce heterocycle substituted monoenes or dienes. For instance the ring could be opened in the presence of ammonia to produce an ethylenically unsubstituted amine, for instance to provide allylic amines of the type disclosed in EP-A-0187390. Substituents in the cyclopropane ring could be further reacted to provide a wide range of useful compounds.

According to a further aspect of the invention there is provided a new process in which a diazirine compound of the formula I',

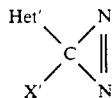

in which Het' represents an optionally substituted aromatic heterocycle attached via ring carbon atom, and X' is halogen, an alkoxy or a cyano group is subjected to thermolytic or photolytic degradation in the presence of an ethylenically unsaturated compound to produce the cyclopropane derivative.

The reaction is most conveniently the thermolytic decomposition of the diazirine compound. The reaction is generally carried out in the presence of excess of the ethylenically unsaturated compound in order to minimise side reactions, for instance dimerization with the release of nitrogen to produce an azine. The olefinic compound is preferably used in at least a five fold excess, preferably at least an eight fold excess. Excess olefinic reagent can be removed, for instance by distillation. The process is preferably also carried out in the presence of a non-polar solvent, which again reduces the production of the azine dimers.

The thermolysis reaction is carried out in a similar manner to the known thermolysis reactions described by Schmitz, Doyle and Liu op cit.

In the process, in a compound of the formula I', X' preferably represents a halogen atom, preferably bromine or, most preferably, chlorine. The halodiazirine compounds produce products which are easily further reacted e.g. by removal or exchange of the halogen and so are preferred for use in the process. X can also be any of the other groups mentioned above, e.g. amino, or, preferably alkoxy or cyano.

The process is found to be of particular value where Het is 2-thienyl.

In the process the ethylenically unsaturated compound used may have a single ethylenic bond or may have two or more such bonds. The compound may be represented generally by the formula II:

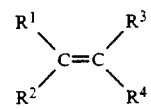

in which R¹, R², R³, R⁴ are each independently selected from hydrogen, halogen, alkyl, alkoxy, alkenyl, alkynyl, aryl, aryloxy, aralkyl, alkaryl, carboxyl, carboxyalkyl cyano, acetylamino and alkylamino, or R¹ and R³ or R² and R⁴ together may represent a C₂ or higher alkylene group, in which any of the alkyl or aryl groups may be unsubstituted or substituted by halogen, alkoxy, aryloxy, hydroxy, carboxy, carboxyalkyl, nitro or an amino group.

A particularly preferred range of ethylenically unsaturated compounds includes C₃₋₆ alkenes, for instance propene, isobutylene, cis- and trans-but-2-ene, 2-methyl-but-2-ene, 2-3-dimethyl-but-2-ene and n-butylene, as well as C₄₋₅ alk-dienes, for instance 1,3-butadiene and isoprene, as well as aralkene compounds such as styrene and stilbene, and also unsubstituted aliphatic carboxylic acids, for instance monocarboxylic acids such as acrylates, including acrylic acid derivatives, methacrylic acid derivatives and crotonic acid derivatives, as well as unsubstituted aliphatic dicarboxylic acids such as any of the carboxylic acid derivatives preferably being esters, usually lower alkyl esters, as well as other olefinic compounds substituted by halogen atoms and/or cyano groups, and cycloalkene compounds such as cyclohexene.

According to a further aspect of the invention there is provided a novel process in which a compound of the formula III:

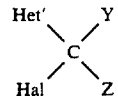

in which Het' has the definition given above in connection with formula I', Hal respresents a halogen atom, preferably bromine, most preferably chlorine, and, either:

a) Y and Z together represent —N=N— or
b) Y is Hal and Z is hydrogen, is reacted under carbene generating conditions in the presence of an ethylenically unsaturated compound selected from monoalkenes having substituents selected from halogen atoms cyano groups, and aryl groups cycloalkenes, monounsaturated aliphatic mono- and di-carboxylic acids and derivatives, and alk-1,3-dienes.

Where the compound of the formula III is a diazirine compound (Y and Z together are —N=N—) the carbene is generated in a thermolytic or photolytic reaction, of the type described above. It is preferred to start with the diazirine compound when the ethylenically unsaturated compound is base-sensitive, for instance when it is an ester of an unsaturated carboxylic acid.

Where the starting material is a heteroaryldihalomethyl compound the carbene-producing reaction is a base induced alpha-elimination using potassium t-butoxide in the presence of a crown ether, or by potassium hydroxide in the presence of a quaternary ammonium compound such as triethylbenzineammonium chloride, for instance as described by Dolgii et al., op. cit. Other descriptions of carbene generation by this route are described in "Carbenes" Eds, Jones and Moss Vols. 1 and 2 and in "Carbene Chemistry" by W. Kirmse Second Edition (1971). This route is often preferred for olefins which are not sensitive to the conditions used to generate the carbene, i.e. when they are not base sensitive. It may thus be preferred for reactions in which the ethylenically unsaturated compound is not an ester of an unsaturated aliphatic carboxylic acid.

Reaction of the carbene with many of the ethylenically unsaturated compounds yields two isomers, the syn- and anti- isomers, these being produced in varying ratios depending on the selectivity of the carbene. Generally the isomers can be separated by chromatography although it has been found that chromatography on silica can result in decomposition of the less stable isomer so that only one isomer is obtained.

Many of the compounds which are produced by the latter novel process are themselves novel. Accordingly in another aspect of the invention there are provided new compounds of the formula IV:

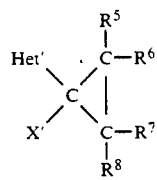

wherein Het' represents an optionally substituted aromatic heterocycle attached via a ring carbon atom and $R^5$-$R^8$ are independently selected from hydrogen, halogen, alkyl, alkenyl, aryl, carboxy, carboxyalkyl and cyano, or $R^6$ and $R^7$ together represent $C_3$ or $C_4$-$\alpha,\omega$-alkylene, provided that at least one of $R^5$ to $R^8$ is other than hydrogen or methyl.

The heteroaryl group Het may be unsubstituted or substituted by one or more groups selected from halogen atoms, alkyl, alkoxy, aryl, aryloxy, alkaryl and aralkyl, any alkyl or aryl groups being substituted or unsubstituted. Particularly preferred compounds are thienyl compounds, especially unsubstituted 2- and 3-thienyl derivatives and pyridyl derivatives.

In one group of compounds of the formula IV at least one of $R^5$ to $R^8$ is a carboxyl group or a derivative, e.g. a carboxylalkyl group. Any or all of the other groups may be hydrogen or may be independently selected from halogen, usually chlorine, and lower alkyl, usually methyl.

The novel compounds may be useful in their own right by virtue of the heteroaryl group and/or the cyclopropane group, or may be used as intermediates in the generation of other active compounds, in which the cyclopropane group is retained and any or all of the groups Hal and $R^5$ to $R^8$ are replaced, or in which the cyclopropane group is converted to a cyclopropene group, or in which the cyclopropane ring is opened and optionally subsequently further reacted.

The novel compound may for instance be reductively dehalogenated to replace the Hal group with a hydrogen atom. Where one of the ring substituents is a carboxyalkyl group that group may be reduced to form the corresponding alcohol which may be used as an intermediate in the production of the fungicidal cyclopropanes described in GB-A-2,192,631.

The following examples illustrate the invention.

EXPERIMENTAL DETAILS

Petroleum refers to the fraction boiling at 40°-60° C. Reagents obtained commercially were used without further purification unless otherwise stated. n-Butyl lithium was obtained from Aldrich Chemical Company as a ca. 1.5M solution in hexane. The accurate molarity was determined titration and diphenylacetic acid. All manipulations involving alkyl lithiums were conducted under a nitrogen atmosphere. Organic solutions were dried using anydrous magnesium sulphate and solvents generally removed on a rotary evaporator at ca. 14 mmHg. T.l.c. was performed on Schleicher and Shuell F 1500 LS 254 silica-gel plates. Medium pressure chromatography was conducted using Merck 7736 silica gel and gravity chromatography using gravity silica or Brockmann activity II alumina.

Melting points were determined using a Kofler hot stage apparatus and are uncorrected. Elemental analysis was determined with a Carlo-Erba Instrumentazione model 1106 elemental analyser. Infra red spectra were recorded as thin film (liquids) or a potassium bromide disc (solids), on a Nicolet 20 SX B Fourier transform spetrometer and the type of absorption (strong, medium or weak) is quoted in the text. $^1$H N.m.r. spectra were recorded at 60 MHz using a Hitachi Perking Elmer R-24B spectrometer, at 200 MHz on a Bruker WP 200, or at 300 MHz using a Bruker WP 300-WB instrument. The order of citation in parenthesis in the text is: number of nuclei (by integration), muliplicity and coupling constant. The abbreviation $W_{\frac{1}{2}}$ refers to the width at half height of a broad signal and unless otherwise stated, spectra were recorded at 60 MHz. Mass spectra, electron impact were obtained using an AEI MS9 or Kratos MS 80RF spectrometer. Peaks and mass measurements refer to the isotopes $^{79}$BR and $^{35}$Cl where applicable.

3-Ethylthiophene was obtained from Synthetic Chemicals Ltd., and contained ca. 17% of the 2,3-dimethylisomer.

EXAMPLE 1

3-Chloro-3-(thien-3-yl)-3H-1,2-diazirine (compound 1,Het=thien-3-yl, X=Cl)

3-Amidinothiophene hydrochloride (3.00 g, 18.5 mmol) and lithium chloride (5 g) were dissolved in dimethyl sulphoxide (50 ml) with stirring. When the solution became clear, petroleum (50 ml) was added. Aqueous sodium hypochlorite (200 ml, 1.2M) containing dissolved sodium chloride (20 g) was then added rapidly so the temperature of the reaction mixture increased to 50° C. Rapid stirring was continued for 45 min at 40°-45° C. with warming if necessary. The petroleum extract was separated and the aqueous solution extracted with petroleum (3×40ml). The combined petroleum extracts were washed with water (200 ml), dried, and the solvent removed to yield the product as a clear orange oil (2.05 g, 70%). Chromatography on silica eluting with light petroleum afforded 3-chloro-3-(thien-3-yl)diazirine (1.79g, 61%) as a pale green oil which was pure by n.m.r. and t.l.c. ($R_f$=0.9; petroleum) which showed $\nu_{max}$ (film) 781s, 847m, 1039m, 1572s (N=N) and 3113w cm$^{-1}$ (the maximum at 1572cm$^{-1}$ is a characteristic N=N stretch); $\delta_H$ (200 MHz; CDCl$_3$) 6.75 (1H, dd, J 1.5, 5.0 Hz), 7.12 (1H, dd, J 1.5, 3.0 Hz), 7.35 (1H, dd, J 3.0, 5.0, Hz); m/z 130, (M$^+$-N$_2$), 95 (M$^+$-N and Cl).

On standing for 5 weeks at −10° C., the neat product darkened slightly and a small amount of yellow solid (ca. 5%) was precipitated. The oil was shown by n.m.r. to be pure diazirine; the solid was removed and recrystallized from light petroleum to afford bright yellow plates characterised as 1,4-dichloro-1,4-di(thien-3-yl)-2,3-diazabuta-1,3-diene (Found: C,41.2; H, 2.0; N, 9.5. C$_{10}$H$_6$N$_2$S$_2$Cl$_2$ requires C, 41.5; H, 2.1; N, 9.7%) which showed $\nu_{max}$ (KBr) 651s, 792s, 849s, 971m, 1231s, 1601s and 3100m cm$^{-1}$; $\delta$H (CDCl$_3$) 7.28 (2H, dd, J 3.0, 4.5 Hz), 7.61 (2H, dd, J 1.5, 4.5 Hz), 7.92 (2H, dd, J 1.5, 3.0 Hz); m/z 288 (M$^+$), 253 (M$^+$-Cl), 144 (M$^+$-C$_5$H$_3$NSCl).

If the temperature was kept below that described above, substantial quantities of a third product were obtained after extraction of the reaction mixture with dichloromethane. The product was recrystallised from light petroleum-ethyl acetate to afford small needles of N-chloro-3-amidinothiophene (0.92 g, 31%), m.p. 96°-98° C. (Found M$^+$ 159.9874; C, 37.1; H, 3.0; N, 17.1. C$_5$H$_5$N$_2$ClS requires M, 159.9862; C, 37.4; H, 3.1; N, 17.4%) which showed $\nu_{max}$ (KBr) 807s, 1344s, 1568s, 1626s, 3100m, 3283m and 3450m cm$^{-1}$; $\delta_H$ (CDCl$_3$) 5.2-5.9 (2H br s, exchanges with D$_2$O), 7.28 (2H, m), 7.58 (1H, m); m/z 160 (M$^+$), 125 (M$^+$-Cl).

EXAMPLE 2

3-chloro-3-(thien-2-yl)-1,2-diazirine (compound I, Het=thien-2-yl X=Cl)

In a similar manner to example 1 but using 10 mol equivalents of sodium hypochlorite on amidine, 2-amidinothiophene hydrochloride was converted into the diazirine. A reaction temperature of below 30° C. for 30 min. led only to the N-chloroamidine, while allowing the temperature to increase to about 40° C. during the addition gave a mixture of the diazirine and aldehyde, the latter resulting from decomposition of the diazirine in the aqueous reaction medium to give a carbene, which is then trapped by water.

Optimum reaction conditions were found to be about 8 min. at 35° C. followed by about 10 min at 30° C.; extraction into petrol and quickly washing with water, afforded 3-chloro-3-(thiene-2-yl) diazirine in 65% yield as a clear orange oil which was pure by $^1$H n.m.r. and t.l.c., the N-chloro amidine not being extracted under these conditions. The diazirine exhibited a characteristic N=N stretching band in the i.r. spectrum at 1566 cm$^{-1}$ while the $^1$H n.m.r. contained three multiplets at $\delta$6.75, $\delta$6.95 and 7.28. The neat product darkened within minutes at room temperature, decomposing exothermically with the evolution of nitrogen. After ca, 30 min. a black oil solid remained; chromatography afforded bright yellow needles of the azine 1,4-dichloro-1,4-di(-thien-2,3-diazabut-1,3-diene, the $^1$H n.m.r. spectrum of which showed a double doublet at $\delta$7.10, a doublet at $\delta$7.48 and a doublet at $\delta$7.72, each integrating for two protons. The diazirine could be stored for several days at −10° C. when neat, or longer if diluted with a non polar solvent.

EXAMPLE 3

General Method for the preparation of 1-chloro-1-(thien-2-yl)cyclopropanes from low boiling alkenes and 3-chloro-3-(thien-2-yl)diazirine (compound III, Het=thien-2-yl, Hal=Cl, Y and Z =—N=N—)

A freshly prepared solution of the diazirine from example 2 (1.0 g, 6 mmol max.) in carbon tetrachloride (10 ml) was added over 5 min to a stirred solution of an alkene in carbon tetrachloride (30 cm$^3$) at between 60° and 70° C. Alkenes which were liquids at room temperature, namely 2,3-dimethylbut-2-ene (compound II, R$^1$=R$^2$=R$^3$=R$^4$=CH$_3$) and 2-methylbut-e-ene (compound II R$^1$=R$^2$=R$^3$=CH$_3$, R$^2$=R$^3$=H) were present in at least 5-fold excess (30 mmol). The remaining three, trans-but-2-ene (compound II, R$^1$=R$^4$=CH$_3$, R$^2$=R$^3$=H) cis-but-2-ene (compound II, R$^1$=R$^2$=CH$_3$,R$^3$=R$^4$=H), and 2-methylpropene, (compound II, R$^1$=CH$_3$, R$^2$=R$^3$=R$^4$=H) were bubbled slowly through the solution during the experiment. After 15 min at 75° C. the reactant solution was allowed to cool and the volatile solvents were removed to yield crude 1-chloro-1-(thien-2-yl)- cyclopropanes which were distilled at reduced pressure to afford analytically pure samples (except for the tetramethyl adduct which crystallised on standing). Yields quoted are with respect to the amidine hydrochloride and all five neat cyclopropanes slowly decomposed to viscous black oils.

a)
1-Chloro-1-(thien-2-yl)-2,2,3,3-tetramethylcyclopropane

Removal cf the solvent gave a straw coloured syrup (0.86 g, 67%) which was pure by n.m.r. Within minutes the product solidified to large oily crystals, m.p. about 20° C. (Found: M$^+$ 214 0576. C$_{11}$H$_{15}$SCl requires M, 214.0583) which showed $\nu_{max}$ (film) 690s, 808m, 857wm 1378w, 2920m and 2951m cm$^{-1}$; $\delta_H$(CCl$_4$) 1.09 (6H, s), 1.31 (6H, s), 6.85 (2H, m), 7.15 (1H, dd. J 2, 4 Hz); m/z 214 (M+), 199 (M$^+$-CH$_3$), 179 (M$^+$-Cl).

b) 1-Chloro-1-(thien-2-yl)-2,2,3-trimethyl-cyclopropane

Evaporation of the solvent yielded a clear orange oil (0.63 g) which was distilled at reduced pressure (bulb to bulb, oven temperature 60° C. at 0.3 mmHg) to afford the product as a straw coloured syrup (0.42 g, 35%) (anti/syn=1.35) (Found: M$^+$ 200.0442. C$_{10}$H$_{13}$SCl requires M, 200.0426) which showed $\nu_{max}$ (film) 699s, 870m, 1233m, 1377w, 1455m, 2928m and 2952m cm$^{-1}$; $\delta_H$(200 MHz; CDCl$_3$; mixture) anti isomer: 0.93 (3H, s), 1.24 (3H, s), 1.25 (3H, d, J 6.5 Hz), 1.4 (1H, m), (2H, m), 7.20 (1H, dd, J 1.5, 5 Hz); syn isomer: 1.00 (3H, s), 1.10 (3H, d, J 6.5 Hz), 1.4 (1H, m), 1.50 (3H,s), 6.9 (2H, m), 7.28 (1H, dd, J 1.5, 5 Hz); m/z 200 (M$^+$), 185 (M$^+$-CH$_3$), 165 (M$^+$-Cl), 149 (M$^+$-Cl and CH$_3$).

c) 1-Chloro-1-(thien-2-yl)-2,2-dimethylcyclopropane

Removal of the solvent following by Kugelrohr distillation (oven temperature 65° C. at 0.7 mmHg) afforded the product as a clear oil (0.23 g. 21%) (Found: M$^+$, 186.0265. C$_9$H$_{11}$SCl requires M, 186.0270) which showed $\nu_{max}$ (film) 700m, 752m, 1046m, 1119m, 1236m, 2926m and 2954m cm$^{-1}$; $\delta_H$ (CCl$_4$) 0.93 (3H, s), 1.20

(1H, d, J 6 Hz), 1.38 (1H, d, J 6 Hz), 6.80 (2H, m), 7.04 (1H, dd, J d, 5 Hz); m/z 186 (M+), 171 (M+-CH$_3$), 151 (M+-Cl).

d) 1-Chloro-1-(thien-2-yl)-2,3-cis-dimethyl-cyclopropane

Removal of the solvent gave a brown oil (1.05 g). Kugelrohr distillation (oven temperature 80°–90° C. at 1.0 mmHg) yielded a pure product (0.12 g, 19%). The colourless oil was an isomeric mixture of cyclopropanes (anti/syn=1.43) (Found: M+ 186 0261, C$_9$H$_{11}$SCl requires M, 186.0270) which showed $\nu_{max}$ (film) 700s, 766nm 1060w, 1230w, 1450w, 2930m and 2960w cm$^{-1}$; $\delta_H$ (200 MHx; CDCl$_3$; mixture) anti isomer: 1.19 (6H, d, J 6.17 Hz, fine splitting), 1.49 (2H, m) 6.9–7.0 (2H, complex m), 7.15 (1H, dd, J 2, 7 Hz); syn isomer: 1.04 (6H, d, J 6.38 Hz, fine splitting), 1.82 (2H, m), 6.9–7.0 (2H, complex m), 7.31 (1H, dd, J 2, 7 Hz); m/z 186 (M+), 171 (M+-CH$_3$), 151 (M+-Cl).

e) 1-Chloro-1-(thien-2-yl)-2,3-trans-dimethylcyclopropane

Removal of the solvent gave a brown oil (0.38 g) which was purified by Kugelrohr distallation (oven temperature 60° C. at 0.8 mmHg) affording a clear orange liquid (0.15 g, 14%) (Found: M+ 186.0265 C$_9$H$_{11}$SCl requires M, 186.0270) which showed $\nu_{max}$ (film) 701s, 776m, 1150m, 1440m, 2929m, 2960m cm$^{-1}$; $\delta_H$ (200 MHz; CDCl$_3$)0.92 (3H, d, J 5.8 Hz), 1.2–1.6 (2H, complex m), 1.39 (3H, d, J 5.8 Hz)), 6.95 (2H, complex m), 7.20 (1H, dd, J 5, 2 Hz); m/z 186 (M+), 171 (M+-CH$_3$), 151 (M+-Cl), 131 (M+-C$_4$H$_8$).

EXAMPLE 4

Thermal decomposition of 3-chloro-3-(2-thien-2-yl) diazirine with other unsaturated compounds.

a) 1-Chloro-1-(thien-2-yl)-2-phenylcyclopropane (compound IV, R$^1$=R$^2$=R$^3$=H, R$^4$=phenyl, Het$^1$=thien-2-yl, Hal=Cl)

A stirred solution of the diazirine from example 2 (1.0 g, 6.4 mmol) in styrene (5.7 g, 55 mmol) was heated to 70° C. for 10 min. Removal of the excess alkene yielded a clear orange/brown oil shown by n.m.r. to be an isomeric mixture of cyclopropanes (syn/anti=2.7). The crude product was purified by silica gel chromatography with light petroleum-ethyl acetate (4:1) as eluent to afford a clear orange syrup identified as an isomeric mixture (syn/anti=2.7) of 1-chloro-1-(thien-2-yl)-2-phenylcyclopropanes (0.70 g, 47%). On standing for a few days, large clear orange crystals were deposited in this syrup and identified as the syn isomer, m.p. 61°–63° C. (Found: M+ 234.0277. Cl$_3$H$_{11}$SCl requires 234.0270) which showed $\nu_{max}$ (KBr) 693s, 710s, 771m, 830m, 1120m, 1500m, 1600m and 3000m cm$^{-1}$; $\delta_H$ (200 MHz; CDCl$_3$) 2.00 (2H, d, J 9 Hz), 3.03 (1H, t, J 9 Hz), 6.74 (1H, dd, J 3.6, 5.0 Hz), 6.81 (1H, dd, J 1.3, 3.6 Hz), 6.96 (1H, dd, J 1.3, 5.0 Hz), 7.1 (5H, m); m/z 234 (M+), 199 (M+-Cl).

The remaining oil contained a mixture of syn and anti isomers in similar proportions. By subtracting the absorbances due to the syn isomer, the anti isomer showed $\delta_H$(200 MHz; CDCl$_3$; mixture) anti isomer: 1.92 (2H, d, J 9 Hz), 2.74 (1H, dd, J 9 Hz), 6.9–7.2 (3H, m), 7.33 (5H, m).

b) 1-Chloro-1-(thien-2-yl)-2-vinyl-2-methyl-cyclopropane (compound IV, R$^5$=R$^6$=H, R$^7$=CH$_3$, R$^8$=vinyl, Het'=thien-2-yl, Hal=Cl)

A stirred solution of the diazirine (0.75 g, 4.7 mmol) and 2-methylbuta-1,3-diene (4.0 g, 59 mmol) in carbon tetrachloride (10 ml) was heated at 40° C. for 30 min. The solution was then filtered and the solvent evaporated to leave a dark oil (1.06 g) which consisted of one major isomer (n.m.r.). Rapid chromatography through a small bed of silica with light petroleum-ethyl acetate (5:1) as eluant afforded a single product showing one spot on t.l.c. (Petrol; R$_f$ 0.8) and identified as anti-1-chloro-1-(thien-2-yl)-2-vinyl-2-methylcyclopropane (0.44 g, 47%), a clear dark oil (Found: M+ 198.0262. C$_{10}$H$_{11}$SCl requires M, 198.0270) which showed $\nu_{max}$ (film) 703s, 908m, 992m, 1082m, 1233m, 1429m, 1595m, 1637m, 2877m, 2929m, 2961m and 3088w cm$^{-1}$; $\delta_H$(200 MHz; CDCl$_3$) 1.05 (3H, s), 1.6 (2H, narrow m), 5.23 (1H, d, J 17.1 Hz), 5.25 (1H, d, J 10.8 Hz), 6.06 (1H, dd, J 10.8, 17.1 Hz), 6.92 (1H, dd, J 3.55, 5.11 Hz), 7.00 (1H, m), 7.25 (1H, m); m/z 198 (M$^{30}$), 183 (M+-CH$_3$), 163 (M+-Cl).

c) 7-Chloro-7-(thien-2-yl)norcarane) (Compound IV, R$^5$=R$^8$=H, R$^6$ and R$^7$=(CH$_2$)$_4$, Het'=thien-2-yl, Hal=Cl)

The diazirine (0.60 g), 3.8 mmol) in cyclohexene (20 cm$^3$, 0.2 mol) was heated at 40°–60° C. for 2 h. After evaporating the solvent, the crude product, a mixture of isomers, was rapidly chromatographed on silica with light petroleum as eluant. Decomposition occured during chromatography, however a single isomer was eluted and identified as pure anti-7-chloro-7-(thien-2-yl)-norcarane (0.22 g, 27%), a colourless oil (Found: M+ 212.0440. C$_{11}$H$_{13}$SCl requires M, 212.0246) which showed $\nu_{max}$ (film) 695s, 769m, 967w, 1243w, 1443m, 2856m and 2938s cm$^{-1}$; $\delta_H$ (200 MHz; CDCl$_3$) 1.2–1.5 (4H, m), 1.6 (2H, narrow m), 1.8 (2H, m) 2.1 (2H,m), 6.86 (1H, dd, J 3.6, 5.0 Hz), 6.91 (1H, J 1.5, 3.6), 7.11 (1H, dd J 1.5, 5.0 Hz); m/z 212 (M+), 177 (M+-Cl).

d) Methyl 2-chloro-2-(thien-2-yl)cyclopropanecarboxylate (Compound IV, R$^5$=R$^6$=R$^7$=R=H, R$^8$=COOCH$_3$, Het'=thien-2-yl, Hal=Cl)

A stirred solution of the diazirine (1.50 g, 9.5 mmol) in methyl acrylate (8.0 g, 90 mmol) and tetrachloroethene (10ml) was heated at reflux for 20 min. The solvents were removed to leave the crude product as a dark oil consisting of an isomeric mixture of cyclopropanes (syn/anti=3.8). Chromatography on silica with light petroleum-ethyl acetate (5:1) as eluent afforded the title compound as a clear orange oil (1.4 g, 68%) with no change in the isomer ratio (Found: M+ 216.0024. C$_9$H$_9$SO$_2$Cl requires M, 216.0012) which showed $\nu_{max}$ (film) 733s, 910m, 1208m, 1676m and 1735s cm$^{-1}$; $\delta_H$ (200 MHz; CDCl$_3$; mixture) major (syn) isomer: 1.90 (1H, dd, J 6.36, 9.18 Hz), 2.18 (1H, dd, J 6.36, 7.06 Hz) 2.65 (1H, dd, J 7.06, 9.18 Hz), 3.55 (3H, s), 6.90 (1H, dd, J 3.60, 5.16 Hz), 7.08 (1H, dd, J 1.27, 3.60), 7.27 (1H, dd, J 1.27, 5.16 Hz); minor (anti) isomer: 1.83 (1H, dd, J 6.41, 9.10 Hz), 2.15 (1H, dd, J 6.41, 7.43 Hz), 2.42 (1H, dd, J 7.43, 9.10 Hz), 3.80 (1H, s), 6.91 (1H, dd, J 3.5, 5.1 Hz), 7.05 (1H, dd, J 1.3, 3.5 Hz), 7.23 (1H, dd, J 1.3, 5.1 Hz); m/z 216 (M+) 181 (M+-Cl), 157 (M+-CO$_2$CH$_3$)

e) Methyl 1-methyl-2-chloro-2-(thien-2-yl) cyclopropanecarboxylate (Compound IV, $R^5=R^6=H$, $R^7=CH_3$, $R^8=COOCH_3$, Het'=thien-2-yl, Hal=Cl)

A stirred solution of (1.30 g, 8.2 mmol) and methyl methacrylate (8.0 g, 80 mmol) in tetrachloroethene (10 ml) was heated at reflux for 20 min. The solvent was removed to yield a brown oil containing the crude cyclopropane (syn/anti=3.0) which was chromatographed on silica eluting with light petroleum ethyl acetate (5:1) to yield methyl 1-methyl-2-chloro-2-(thien-2-yl) cyclopropane carboxylate (1.65 g, 87%) as a clear orange oil with no change in the isomer ratio (Found: $M^+$ 230.0177. $C_{10}H_{11}SO_2Cl$ requires M, 230.0168) which showed $\nu_{max}$ (film) 705m, 1158s, 1298s, 1435m, 1734s, 2950m and 3107w cm$^{-1}$; $\delta_H$ (CCl$_4$; mixture) syn isomer; 1.33 (1H, d, J 6 Hz), 1.64 (3H, s), 2.34 (1H, d, J 6 Hz), 3.28 (3H, s), 6.80 (2H, m), 7.05 (1H, dd, J 2, 5 Hz); anti isomer: 1.47 (1H, d, J 6 Hz), 2.20 (1H, d, J 6 Hz), 1.13 (3H, s), 3.69 (3H, s), 6.70 (2H, m), 7.10 (1H, dd, J 2, 5 Hz); m/z 230 ($M^+$).

f) Methyl 2-chloro-2-(thien-2-yl)-3-methylcyclopropanecarboxylate (Compound IV, $R^5=R^7=H$, $R^6=CH_3$, $R^8=COOCH_3$, Het'=thien-2-yl, Hal=Cl)

The diazirine (0.80 g, 5.0 mmol) in methyl crotonate (3.5 g, 36 mmol) was heated with stirring to 80° C. for 10 min. Excess alkene was removed at reduced pressure to give an oil which consisted of an azine and an isomeric mixture of cyclopropanes (syn/anti=5.3). The product was purified by chromatography on silica with light petroleum-ethyl acetate (4:1) as eluent to afford methyl 2-chloro-2-thien-2-yl)-3-methylcyclopropanecarboxylate (0.35 g, 30%) as a clear red oil, The isomer ratio was identical to that of the crude product (Found: $M^+$ 230.0245. $C_{10}H_{11}SO_2Cl$ requires M, 230.0168) which showed $\nu_{max}$ (film) 704m, 1203m, 1324m, 1440m, and 1737s, cm$^{-1}$; $\delta_H$ (CCl$_4$) syn isomer: 1.48 (3H, d, J 5.5 Hz), 2.0–2.4 (2H, m) 3.44 (3H, s), 6.85 (2H, m), 7.12 (1H, d, J 4 Hz); anti isomer: 1.01 (3H, d, J 5.5 Hz), 2.0–2.4 (2H, m), 3.71 (3H, s), 6.85 (2H, m), 7.12 (1H, d, J 4 Hz); m/z 230 ($M^+$), 195 ($M^+$-Cl), 171 ($M^+$-CO$_2$Me).

g) Methyl 2-chloro-2-(thiphen-2-yl)-3,3-dimethylcyclopropanecarboxylate (Compound IV, $R^5=R^6=CH_3$, $R^7=H$, $R^8=COOCH_3$, Het'=thien-2-yl, Hal=Cl)

A stirred solution of the diazirine (1.00 g, 6.3 mmol) in methyl 3,3-dimethylacrylate (7.0 g, 61 mmol) was heated at 80° C. for 15 min. Excess alkene was removed by vacuum distillation to leave a brown oil consisting of an isomeric mixture of cyclopropanes (syn/anti=3.3). Purification by chromatography on silica with light, petroleum-ethyl acetate (5:1) as elient afforded methyl 2-chloro-2-(thien-2-yl)-3,3-dimethylcyclopropanecarboxylate (0.92 g, 60%) as a clear syrup with no change in the isomer ratio (Found: $M^+$ 244.0326. $C_{11}H_{13}O_2SCl$ requires M, 244.0325) which showed $\nu_{max}$ (film) 704m, 1116s, 1199m, 1741s and 2953m cm$^{-1}$; $\delta_H$ (CDCl$_1$; mixture) syn isomer: 1.33 (3H, s), 1.57 (3H, s), 2.20 (1H, s), 3.60 (3H, s), 6.8 (2H, m), 7.15 (1H, m); anti isomer: 1.03 (3H, s), 1.57 (3H, s), 2.20 (1H, s), 3.60 (3H, s), 6.8 (2H, m) and 7.15 (1H, m); m/z 244 ($M^+$), 209 ($M^+$-Cl).

h) 1,2-Dichloro-2-(thien-2-yl)cyclopropane-carbonitrile (Compound IV, $R^5=R^6=H$, $R^7=Cl$, $R^8=CN$, Het'=thien-2-yl, Hal=Cl)

A stirred solution of the diazirine (1.50 g, 9.5 mmol) and α-chloroacrylonitrile (8.0 g, 92 mmol) in tetrachloroethane (10 ml) was heated at reflux for 20 min. The solvents were removed to leave the crude cyclopropane as a black oil with a isomer ratio of 1:1. Chromatography on silica with light petroleum-ethyl acetate (5:1) as eluent yielded 1,2-dichloro-2-(thien-2-yl)cyclopropanecarbonitrile (1.75 g, 84%) as a clear orange oil with no change in the isomer ratio (Found: $M^+$ 216.9533. $C_8H_5NSCl$ requires M, 216.9520) which showed $\delta_H$ (CCl$_4$; mixture) syn isomer: 2.00 (1H, d, J 9 Hz), 2.63 (1H, d, J 9 Hz), 6.9 (2H, m), 7.28 (1H, d, J 5 Hz); anti isomer: 2.22 (1H, d, J 9 Hz), 2.40 (1H, d, J 9 Hz), 6.9 (2H, m), 7.28 (1H, d, J 9 Hz); m/z 217 ($M^+$), 182 ($M^+$-Cl).

The material decomposed to a black oil on standing for several hours at room temperature.

EXAMPLE 5

Methyl 2-chloro-2-(thien-3-yl)-3,3-dimethylcyclopropanecarboxylate (Compound IV, $R^5=R^6=CH_3$, $R^7=H$, $R^8=COOCH_3$, Het'=thien-3-yl, Hal=Cl)

A stirred solution of the diazirine produced in Example 1 (0.30 g, 1.9 mmol) and methyl 3,3-dimethylacrylate (Compound II $R^1=R^2=CH_3$, $R^3=H$, $R^4=COOCH_3$), (1.7 g, 15 mmol) in carbon tetrachloride (2 ml) was heated at 60°–80° C. for 1 h. The solvent was removed to give an isomeric mixture of cyclopropanes (syn/anti=2.2). Chromatography on silica afforded the product as a clear orange oil (0.30 g, 65%) with no change in the isomer ratio (Found: $M^+$, 244 0356. $C_{11}H_{13}SO_2Cl$ requires M, 244.0324) which showed $\nu_{max}$ (film) 784m, 1117w, 1162s, 1377m, 1438s, 1740s, 2877w, 2929w, 2954m and 3109w cm$^{-1}$; $\delta_H$ (200 Mz; CDCl$_3$) major isomer: 1.31 (3H, s), 1.60 (3H, s), 2.23 (1H, s), 3.67 (3H, s), 6.99 (1H, dd, J 1.4, 4.9 Hz), 7.25 (2H, m); minor isomer: 0.99 (3H, s), 1.60 (3H, s), 2.20 (1H, s), 3.76 (3H, s), 7.11 (1H, dd, J 1.5, 4.9 Hz), 7.25 (2H, m); m/z 244 ($M^+$), 229 ($M^+$-Cl).

EXAMPLE 6

Preparation of 1-bromo-1-(2,5-dibromothien-3-yl) cyclopropanes from 2,5-dibromo-3-dibromomethyl thiophene (compound III, Het=2,5-dibromothien-3-yl, Hal=Y=Br, Z=H)

General procedure

Potassium-t-butoxide (2.2 g, 20 mmol) was added over 5 min to a rapidly stirred solution of 2,5-dibromo-3-dibromomethylthiophene (produced by bromination of 3-methylthiophene) (2.0 g, 4.8 mmol) and excess alkene in dry ether (20 cm$^3$) at 0° C. The higher boiling alkenes (styrene, 2,3-dimethylbut-2-ene and 2-methylbut-2-ene) were present in ≧6-fold excess whereas for lower boiling alkenes, a stream of gas was bubbled through a solution of the dibromomethylthiene in ether (20 ml) at 0° C. until an increase of ca. 5 ml was observed. The reaction was shown by n.m.r. to be 70% complete after 10 min at 0° C. After vigorous stirring for a further 20 min at 20° C., the gelatinous mixture was poured onto water (100 ml) and extracted with light petroleum (20 ml). The organic extract was washed with water (3×30ml), dried, and the solvent removed. The products were purified by chromatography on silica (prewashed with triethylamine) eluting with light petroleum. Isomer ratios were determined by 200 MHz $^1$H n.m.r. of the crude products.

a)
1-Bromo-1-(2,5-dibromothien-3-yl)-2,2,3,3-tetramethylcyclopropane

Using the above method 2,3-dimethylbut-2-ene (3.2 g, 38 mmol) and the dibromomethylthiophene (2.0 g 4.8 mmol) gave a viscous oil which solidified on standing for 24 h. Recrystallisation from petroleum at ca. $-20°$ C. afforded the title compound as a pale yellow powder (1.69 g, 84%), m.p. 78°-80° C. (Found M$^+$: 413.8317; C, 31.7; H, 2.7. $C_{11}H_{13}Br_3S$ requires M, 413.8289; C, 31.7; H, 3.1%) which showed $\nu_{max}$(KBr) 731m, 825s, 1376m, 1447w, 2869w, 2917w and 2943w cm$^{-1}$; (200 MHz; CDCl$_3$) 1.11 (3H, s), 1.13 (3H, s), 1.34 (3H, s), 1.40 (3H, s) and 6.87 (1H, s); m/z 414 (M$^+$), 335 (M$^+$-Br), 256 (M$^+$-$^2$Br), 177 (M$^+$-$^3$Br).

b)
1-Bromo-1-(2,5-dibromothien-3-yl)-2,2,3-trimethylcyclopropane

2-Methylbut-2-ene (2.7 g 38 mmol) and the dibromomethylthiophene (2.0 g, 3.8 mmol) gave a red/brown syrup (1.77 g, 91%) which was pure by n.m.r (anti/syn=1). The product was obtained as a clear orange syrup (1.63 g, 84%) after chromatography (Found M$^+$: 399.8101. $C_{10}H_{11}Br_3S$ requires M, 399.8133) which showed $\nu_{max}$(film) 829m, 991s, 1116m, 1454m, 2867m, 2924s and 2953s cm$^{-1}$; $\delta_H$ (200 MHz; CDCl$_3$; mixture) 1.02 (s), 1.3 (br m), 6.84 (1H, s) 6.90 (1H, s); m/z 400 (M$^+$, 321 (M$^+$-Br), 242 (M$^+$-$^2$Br) The $^1$H n.m.r. spectrum contained broad signals due to slow rotation on an n.m.r. time scale.

c)
1-Bromo-1-(2,5-dibromothien-3-yl)-2,2-dimethylcyclopropane

The dibromomethylthiophene (2.04 g, 4.9 mmol) and 2-methylpropene gave a red oil (1.61 g, 85%) which was pure by n.m.r. Chromatography on neutral silica with petroleum as eluent afforded the title compound as a pale yellow oil (1.3, 66%) (Found M$^+$: 385.8007 $C_9H_9Br_3S$ required M, 385.7976) which showed $\nu_{max}$ (film) 659s, 992s, 1062m, 1115m, 1442m, 2924s and 2954s cm$^{-1}$; $\delta_H$(CCl$_4$) 1.02 (3H, s), 1.2 (2H, br m, W 12 Hz), 1.50 (3H, s), 6.77 (1H, s); m/z 386 (M$^+$), 307 (M$^+$-Br), 228 (M$^+$-$^2$Br), 149 (M$^+$-$^3$Br).

d)
1-Bromo-1-(2,5-dibromothien-3-yl)-2,3-cisdimethylcyclopropane

Using the dibromomethylthiophene (2.05 g 5.0 mmol) and cis-but-2-ene gave the cyclopropanes as a clear red syrup (1.63 g, 84%) which was pure by n.m.r. (anti/syn=6.0). Chromatography afforded a clear orange syrup (1.44 g, 74%), with isomer ratio unchanged (Found M$^+$ 385.8014. $C_9H_9Br_3S$ requires M, 385.7976) which showed $\nu_{max}$(film) 710s, 827s, 963s, 1133s, 1184s, 1430m, 2871m, 2927s, 2957m and 2997w cm$^{-1}$; (200 MHz; CDCl$_3$; mixture): ma.lor isomer: 1.21 (8H, s), 6.92 (1H, s); minor isomer 1.04 (6H, d, J 6.5 Hz), 1.2 (2H, m), 6.90 (1H, s); m/z 386 (M$^+$), 307 (M$^+$-Br), 228 (M+2Br), 149 (M$^+$-$^3$Br)

On standing for several months at $-10°$ C., a sample of the neat product solidified. Crystallisation from methanol afforded the major (anti) isomer as colourless platelets, m.p. 60°-61° C. (Found C, 27.7; H, 2.2. $C_9H_9SBr_3$ requires C, 27.8; H, 2.3%) which showed $\delta_H$ (CCl$_4$) 1.18 (8H, s), 6.75 (1H, s).

e)
1-Bromo-1-(2,5-dibromothien-3-yl)-2,3-transdimethylcyclopropane

Using the dibromomethylthiophene (2.03 g 4.9 mmol) and trans-but-2-ene gave a clear red syrup (1.50 g, 83%) which was pure by n.m.r. Chromatography on neutral silica with light petroleum as eluent afforded the cyclopropane as a clear yellow syrup (1.34 g, 70%) (Found M$^+$ 385.7910 $C_9H_9Br_3S$ requires M, 385.7976) which showed $\nu_{max}$ (film) 729s, 1002s, 1136s, 1449s, 2867m, 2926s and 2958s cm$^{-1}$; $\delta_H$(200 MHz; CDCl$_3$) 0.81 (1H, quintet, J 6.3 Hz), 1.00 (3H, d, J 6.3 Hz), 1.30 (1H, quintet, J 6.3 Hz), 1.44 (3H, d, J 6.3 Hz), 6.91 (1H, s); m/z 386 (M$^+$) 307 (M$^+$-Br), 228 (M$^+$-2Br), 149 (M$^+$-3Br).

f)
1-Bromo-1-(2,5-dibromothien-3-yl)-2-vinyl-2-methylcyclopropane

The dibromomethylthiophene (compound IV, $R^5=R^6=H$, $R^7=CH_3$ $R^8=$vinyl, Het=2,5-thien-3-yl, Hal=Br) (2.55 g, 6.2 mmol) and 2-methylbuta-1,3-diene (compound II, $R^1=R^2=H$, $R^3=CH_3$, $R^4=$vinyl) (4.2 g, 62 mmol) as above afforded an orange oil (2.2 g, 8µ90%) which consisted of two diastereoisomers in a 1:1 ratio. Chromatography on silica (light petroleum eluent) yielded three fractions. The first was syn-1-bromo-1-(2,5-dibromo-thien-3-yl)-2-vinyl-2-methylcyclopropane (0.53 g, 21%) (Found M$^+$-Br: 318.8820. $C_{10}H_9SBr_2$ requires M-Br, 318.8792) which showed $\nu_{max}$ (film) 909m, 995s, 1417m, 1633w, 2927w and 2960w cm$^{-1}$: $\delta_H$ (CCl$_4$) 1.40 (1H, d, J 6 Hz), 1.58 (3H, s), 1.70 (1H, d, J 6 Hz), 5.0 (3H, m), 6.7 (1H, s); $\delta_H$(200 MHz; CDCl$_3$) 1.45 (1H, br m), 1.63 (3H, s), 1.7 (1H, br m), 5.11 (3H, br m), 6.86 (1H, s) (The signals in the 200 MHZ $^1$H n.m.r. spectrum were broad due to slow rotation); m/z 319 (M$^+$-Br), 240 (M+2Br). The second fraction (1.38 g, 56%) was a mixture of isomers (anti/syn=1.5), while the third fraction was the anti-isomer (70 mg, 3%) which showed $\nu_{max}$ (film) 909s, 994s, 1080m, 1418m, 1634w and 2965m cm$^{-1}$; $\delta_H$(CCl$_4$) 1.10 (3H, s)s, 1.55 (2H, br m, W$_{\frac{1}{2}}$ 12 Hz), 5.07 (1H, d, J 17 Hz), 5.15 (1H, d, J 10 Hz), 5.97 (1H, dd, J, 10, 17 Hz), 6.79 (1H, s); m/z 319 (M$^+$-Br), (M$^+$-2Br). The first compound was characterised as the syn-isomer because the methyl singlet at $\delta$1.40, was downfield from that of the second, anti-isomer at $\delta$1.10 which is shielded by the cis-related thiene ring. The olefinic hydrogens of the syn-isomer appeared as a narrow multiplet centered at $\delta$5.0 whereas the olefinic hydrogens of the anti-isomer displayed a typical vinyl group pattern. This may be explained by assuming that H$_1$ of the syn-isomer experiences greater shielding by the cis-related thiene ring than do the terminal olefinic protons.

g)
1-Bromo-1-(2,5-dibromo-thien-3-yl)-2-phenylcyclopropane (Compound IV, $R^5=R^6=R^7=H$, $R^8=$phenyl, Het'=2,5-dibromothien-3-yl, Hal=Br) (3.0 g 7.2 mmol) and styrene (4.5 g, 44 mmol, 6 equiv.) gave a red syrup (2.7 g 85%) (syn/anti=5). Chromatography over neutral silica with petroleum as eluent afforded the pure major (syn) isomer, as a colourless viscous syrup (1.13 g, 36%) which solidified on standing and was recrystallised from petroleum-ether to yield colourless needles, m.p. 71°–73° C. (Found: C, 35.8; H, 2.0. $C_{13}H_9SBr_3$ requires C, 35.7; H, 2.1%) which showed $\nu_{max}$ (film) 705s, 773m, 999m, 1117w, 1497w, 3031w and 3087w cm$^{-1}$; $\delta_H$ (200 MHz; CDCl$_3$) 1.89 (1H, t, J 7.35 Hz), 2.04 (1H, dd, J 7.35, 10.0 Hz), 2.98 (1H, dd, J 7.6, 10 Hz), 6.55 (1H, s), 6.85 (2H, complex m), 7.10 (3H, m); m/z 434 (M$^+$). Continued elution yielded a mixture of both isomers (0.70 g, 22%) (syn/anti=2). By subtracting the absorbances due to the major isomer, the minor isomer showed $\delta_H$ (200 MHz; CDCl$_3$; mixture) anti isomer: 1.8 (2H, m), 2.50 (1H, dd, J 8 Hz, 10 Hz), 7.06 (1H, s), 7.30 (5H, m). On the basis of $^1$H n.m.r. spectroscopy the major isomer was assigned as the syn-isomer since the phenyl hydrogens at $\delta$6.8 (2H) and $\delta$7.1 (3H) resonated upfield from those of the minor isomer (which appeared as a narrow multiplet at $\delta$7.4) due to shielding by the thiene ring.

EXAMPLE 7 i) 3-Dichloromethylthiophene

3-Thiophenecarboxaldehyde (10.0 g, 89 mmol) in ether (30 ml) was added dropwise to a stirred suspension of phosphorus pentachloride (20 g, 96 mmol) in ether (100 ml). After 15 min at 0° C. the clear solution was poured onto ice-water, washed with saturated sodium hydrogen carbonate solution (2×100 ml) followed by water (100 ml), and dried. Removal of the solvent yielded pure 3-dichloromethylthiophene (12.2 g, 82%) as a clear pale yellow oil (Found M$^+$ 165.9406. $C_5H_4SCl_2$ requres M, 165.9410) which showed $\nu_{max}$ (film) 715s, 771m, 834m, 1153m, 1421m, 1690w and 3110m cm$^{-1}$; $\delta_H$ (CCl$_4$) 6.67 (1H, s), 7.18 (2H, narrow m), 7.30 (1H, narrow m); m/z 166 (M$^+$), 433 (M$^+$-Cl).

The product could be stored either neat or in solution at room temperature without decomposition.

ii) Preparation of 1-chloro-1-(thien-3-yl)cyclopropanes from 3-dichloromethylthiophene (Compound III, Het=thien-3-yl, Hal=Y=Cl, Z=H)

In a typical experiment, potassium-t-butoxide (2.0 g, 18 mmol) was added over 5 min to a rapidly stirred solution of 3-dichloromethylthiophene produced as in i) (1.00 g 6.0 mmol) in dry ether (10–20 ml) at 0° C., containing an excess of alkene (>8 equiv.) as in the general procedure of Example 6. Cyclohexene was present in 20-fold excess. After 1 h at 20° C., the products were worked up as above to give oils which contained no starting material, although traces of t-butanol were present. The crude cyclopropanes were purified by chromatography and/or vacuum distillation. Both methods caused some loss of yield.

a)
1-Chloro-1-(thien-3-yl)-2,2,3,3-tetramethylcyclopropane 2,3-Dimethylbut-2-ene gave a product which solidifed on standing and was recrystallised from light petroleum at ca. −20° C. to give a pale yellow solid (0.81 g, 63%), m.p. 58°–60° C. (Found M$^+$ 214.0560 $C_{11}H_{15}SCl$ requires M, 214.0583) which showed $\nu_{max}$ (film) 770s, 1378m, 2872s, 2922s, 2951s, 3005m and 3099w cm$^{-1}$; $\delta_H$(CDCl$_3$) 1.05 (6H, s), 1.32 (6H, s), 6.95 (1H, dd, J 3, 5 Hz), 7.06 (2H. m); m/z 214, (M$^+$), 199 (M$^+$-CH$_3$), 179 (M$^+$-Cl).

b) 1-Chloro-1-(thien-3-yl)-2,2,3-trimethylcyclopropane

2-Methylbut-2-ene gave a mixture of geometrical isomers (anti/syn=1.31) (0.7 g, 59%). Kugelrohr distillation (oven temperature 80° C. at 0.1 mmHg) afforded the product as a colourless oil (0.47 g, 40%) with no change in the isomer ratio (Found M$^-$ 200.0431 $C_{10}H_{13}SCl$ requires M, 200.0426). Chromatography on silica with petroleum as eluent resulted in decomposition of the minor (syn) isomer affording pure major anti-isomer (27%) (Found M$^+$ 200.0437. $C_{10}H_{13}SCl$ requires M, 200.0426) which showed $\nu_{max}$ (film) 752s, 773s, 838s, 1453m, 2927s, 2950s and 2996m cm$^{-1}$; $\delta_H$ (200 MHz; CDCl$_3$) 0.85 (3H, s), 1.22 (3H, s), 1.24 (4H, m), 7.11 (2H, m), 7.24 (1H, q, J 3, 5 Hz); m/z 200 (M$^+$), 185 (M$^+$-CH$_3$), 165 (M$^+$-Cl). From the $^1$H n.m.r. of the mixture, the minor (syn) isomer showed $\delta_H$ (200 Mz; CDCl$_3$) 0.94 (3H, s), 1.05 (3H, d, J 6.5 Hz), 1.35 (1H, q, J 6.5 Hz), 1.48 (3H, s), 7.05 (1H, dd, J 1.5, 5.0 Hz) and 7.25 (2H,m); m/z 200 (M$^+$), 185 (M$^+$-CH$_3$), 165 (M$^+$-Cl).

c) 1-Chloro-1-(thien-3-yl)-2,2-dimethylcyclopropane

2-Methylpropene gave the title compound which was purified by chromatography over a small amount of silica to yield a clear pale green oil (0.53 g, 47%). Kugelrohr distillation at reduced pressure gave a pure yield of 29% (oven temperature 82° C. at 0.5 mmHg) (Found M$^+$ 186.0299. $C_9H_{11}SCl$ requires M, 186.0270) which showed $\nu_{max}$ 2982m cm$^{-1}$; $\delta_H$ (CCl$_4$) 0.82 (3H, s), 1.05 (1H, d, J 6 Hz), 1.40 (1H, d, J 6 Hz), 1.42 (3H, ), 7.0 (3H, m); m/z 186 (M$^+$), 171 (M$^+$-CH$_3$), 151 (M$^+$-Cl).

d)
1-Chloro-1-(thien-3-yl)-2,3-cis-dimethylcyclo-propane

Cis-but-2-ene gave an oil (0.8 g) which was a mixture of cyclopropanes (anti/syn=2.8). Chromatography on alumina with petroleum as eluent afforded a colourless oil (0.39 g, 35%) with no change in the isomer ratio (Found M$^+$ 186.0283. $C_9H_{11}SCl$ requires M, 186.0270) which showed $\nu_{max}$ (film) 760s, 834m, 1084m, 1386m, 1463m, 2873m, 2930s, 2957m and 3006m cm$^{-1}$; $\delta_H$ (200 MHz; CDCl$_3$; mixture) anti-isomer: 1.18 (6H, d, J 6.2 Hz), 1.38 (2H, m), 6.95 (1H, dd, J 1.5, 5 Hz), 7.15 (1H, dd, J 3, 6 Hz), 7.2 (1H, m); syn isomer 0.98 (6H, d, J 6.4 Hz), 170 (2H, m), 7.08 (1H, dd, J 2, 4.5 Hz), 7.2 (2H, m); m/z 186 (M$^+$), 171 (M$^+$-CH$_3$), 151 (M$^+$-Cl). The major (anti) isomer was obtained pure by selective silver ion catalysed ring opening and methanolysis of the syn isomer.

e)
1-Chloro-1-(thien-3-yl)-2,3-trans-dimethylcyclopropane

Kugelrohr distillation (oven temperature 70° C. at 0.5 mmHg) of the crude product obtained from reaction with trans-but-2-ene afforded the cyclopropane as a colourless oil (0.30 g, 27%) (Found M$^+$ 186.0289. $C_9H_{11}SCl$ requires M, 186.0270) which showed $\nu_{max}$ (film) 745s, 778s, 836m, 954m, 1173m, 1381w, 1451m, 2870m, 2928s and 3006m cm$^{-1}$; $\delta_H$ (200 MHz; CDCl$_3$) 0.86 (3H, d, J 5.9 Hz), 1.18 (2H, m), 1.39 (3H, d, J 5.9 Hz), 7.14 (2H, complex m), 7.26 (1H, dd, J 3, 5 Hz); m/z 186 (M$^+$), 171 (M$^+$-CH$_3$), 151 (M$^+$-Cl).

f) 7-Chloro-7-(thien-3-yl)bicyclo[4.1.0]heptane
(Compound IV, $R^5, R^8=H$, $R^6$ and $R^7=(CH_2)_4$, Het′=thien-3-yl, Hal=Cl)

Cyclohexene (compound II, $R^1=R^3=H$, $R^2$ and $R^4=(CH_2)_4$) (8.0 g, 0.1 mol) gave a brown oil (0.78 g) which was purified by chromatography on silica with petroleum as eluent to afford a colourless oil (0.30 g, 24%). The $^1H$ n.m.r. spectrum of the crude and purified products were identical in the region of the thiene ring protons, indicating an unchanged isomer ratio (anti/syn=1.7) (Found M+ 212 0443. C11H13SCl requires M, 212.0426) which showed $\nu_{max}$ (film) 749m, 783m, 1173m, 1444m, 2857m and 2936s cm$^{-1}$; $\delta_H$ (200 MHz; CDCl3; mixture) major (anti) isomer: 0.6–2.0 (10H, complex m), 6.93 (1H, dd, J 1.4, 5.0 Hz), 7.30 (1H, dd, J 1.4, 3.5Hz), 7.23 (1H, dd, J 3.0, 5.0 Hz); minor (syn) isomer: 0.6–2 (10H, complex m), 7.17 (1H, dd, J 1.3, 5.0 Hz), 7.33 (1H, dd, J 3.0, 5.0 Hz), 7.80 (1H, dd, J 1.3, 3.0 Hz); m/z 212 (M+); 177 (M+-Cl) comparison of the 200 MHz $^1H$ n.m.r. spectrum with that of 1-chloro-1-(thien-3-yl)-2,3-cis-dimethylcyclopropane in the region of the thiene ring protons was made to assign the configurational isomers; in each case the protons of the anti-isomer resonated upfield from those of the syn.

EXAMPLE 8 a) 4-Methyl-3-thiophenecarboxaldehyde

3-Bromo-4-methylthiophene (4.5 g, 25 mmol) in dry ether (15 ml) was added over 5 min to a rapidly stirred solution of n-butyl lithium (30 mmol) in hexane/ether (1:1, 60 ml) at −65° to −70° C. After 30 min. at −70° C., N,N,-dimethylformamide (2.2 g, 30 mmol) in dry ether (10 ml) was added dropwise and the mixture stirred for 2 h at −70° C., followed by warming to 0° C. Hydrochloric acid (50 ml), 2M) was added slowly with stirring and the organic layer was separated. The aqueous solution was extracted with ether (30 ml), and the combined organic extracts were washed with water and dried. Removal of the solvent yielded a clear, pale orange oil shown by n.m.r. to contain three components in a 3:1:1 ratio. Chromatography on silica with light petroleum ethyl acetate (3:1) as eluent gave two major fractions. Distillation of the first at reduced pressure afforded pure 4-methylthiophen-3-carboxaldehyde (1.15 g, 37%) as a colourless oil b.p. 44° C. at 0.5 mmHg (Found M+: 126.0165 C6H60S requires M, 126.0139) which showed $\nu_{max}$ b 806m, 1209m, 1439m, 1532w, 1685s, 2925w and 3095w cm$^{-1}$; $\delta_H$ (CCl4) 2.41 (3H, s), 6.76 (1H, br s, fine splitting), 7.80 (1H, d, J 4 Hz), 9.76 (1H, s); m/z 126 (M+), 125 (M+-H), 97 (M+-CHO). The distillation residue consisted of an oily solid. Recrystallisation several times from light petroleum and ethyl acetate yielded 3-bromo-methylthiophen-2-carboxaldehyde (65 mg, 1.2%), m.p. 58°–60° C. (Found M+ 203 9259. C5H5BrOS requires 203.9359) which showed $\nu_{max}$ (KBr) 606s, 1012s, 1214s, 1435s, 1661s and 3088m cm ; $\delta_H$(CCl4) 2.26 (3H, s), 7.27 (1H, s), 9.84 (1H, s.); m/z 203 (M+). The second was characterised as 4-methyl-2,3-thiophenedicarboxaldehyde. Recrystallisation from light petroleum and ether afforded small needles (ca. 50 mg, 1%, m.p. 70°–71° C. (Found M+:154.0134. C7H6SO2 requires M, 154.0088) which showed $\nu_{max}$ (KBr) 1230s, 1524m, 1656s, and 1679s cm$^{-1}$; $\delta_H$(CCl4) 2.57 (3H, s), 7.29 (1H, s), 10.36 (1H, s), 10.48 (1H, s); m/z 154 (M+), 125 (M+-CHO).

b) 4-Methyl-3-dichloromethylthiophene

4-Methyl-3-thiophenecarboxaldehyde produced as in a) (1.5 g, 12 mmol) in ether (10ml) was added dropwise to a stirred suspension of phosphorus pentachloride (3.0 g, 14 mmol) in dry ether (20ml) as in example 7i). After 30 min at 0° C. followed by 30 min at 20° C., the solution was poured onto ice-water (30cm$^3$) and worked up as in example 7 i) above to give 4-methyl-3-dichloromethylthiophene (2.1 l g, 96%) as a pale yellow oil which was pure by n.m.r. (Found M+: 179.9632. C6H6SCl2 requires M, 179.9566) which showed $\nu_{max}$ (film) 747s, 765s, 1207m, 1455m, 1685w, 2926w and 3103w cm$^{-1}$; $\delta_H$(CCl4) 2.30 (3H, s), 6.64 (1H, s), 6.78 (1H, br s, W 4 Hz), 7.34 (1H, d, J 4 Hz); m/z 180 (M+), 145 (M+-Cl).

c) 1-Chloro-1-(4-methyl-thien-3-yl)-2,2-dimethylcyclopropane

In a process similar to that described in Example 7, potassium-t-butoxide (3.0 g, 26 mmol) was added over 10 min to a vigorously stirred solution of 4-methyl-3-dichloromethylthiophene produced in b) (1.91 g, 11 mmol) and 2-methylpropene (15 cm$^3$, 10 g, 0.2 mol) in dry ether (20 ml) at 0° C. After 30 min at 0° C. the mixture consisted of a brown gelatinous mass. Ether (10 ml) was added and stirring continued for 30 min at 20° C. The mixture was diluted with water (100 ml) and the organic extract separated. The solvent was removed and the residue was take up in petroleum (20 ml), washed with water (4×50 ml) and dried. Removal of the solvent yielded the crude product (1.32 g, 63%) which was distilled at reduced pressure (oven temperature 80° C. at 0/2 mmHg) to afford the cyclopropane as a colourless oil (1.04 g, 49%) (Found M+: 220 0440 C10H13SCL requires M, 200.0426) which showed $\nu_{max}$ (film) 772s, 799s, 1074m, 1452, 2870m, 2926m, 2952m and 2977m: $\delta_H$(CCL4) 0.85 (3H, s), 1.03 (1H, d, J 6 Hz), 1.22 (1H, d, J 6 Hz), 1.46 (3H, s), 2.24 (3H, s), 6.75 (1H, br s, fine splitting), 6.98 (1H, d, J 4 Hz); m/z 200 (M+), 185 (M+-CH3), 165 (M+-Cl)

EXAMPLE 9 a) 2,5-Diethyl-3-thiophenecarboxaldehyde

Titanium tetrachloride (8.0 cm$^3$, 70 mmol) was added slowly under nitrogen to a stirred solution of 2,5-diethylthiophene (6.0 g, 43 mmol) in dichloromethane (25 ml) at 0° C. After 10 min, 1,1-dichloromethyl methyl ether (5.0 g, 43 mmol) was added dropwise causing a vigorous reaction and the evolution of hydrogen chloride. The dark mixture was stirred at 0° C. for 30 min followed by 1 h at 20° C. and then poured onto ice water (100 ml). The organic phase was separated, the aqueous solution was extracted with dichloromethane (3×20ml) and the combined organic extracts were wahsed with 10% aqueous sodium hydroxide (2×50 ml) and dried. Removal of the solvent gave a brown oil which was distilled at reduced pressure to yield 2,5-diethyl-3-thiophenecarboxaldehyde (4.1 g, 57%) as a colourless oil which darkened rapidly, b.p. 72° C. at 0.3 mmHg (Found M+ 168.0620. C9H12SO requires M, 168.0609) which showed $\nu_{max}$ (film) 1195m, 1387m, 1457m, 1676s, 2875m, 2933m and 2970s cm$^{-1}$; $\delta_H$ (CCl4) 1.28 (3H, t, J 8 Hz) 1.32 (3H, t, J 8 Hz), 2.75 (2H, q, J 8 Hz), 3.13 (2H, q, J 8 Hz), 6.93 (1H, s), 9.85 (1H, s); m/z 168 (M+), 153 (M+-CH3), 139 (M+-C2H5).

b) 2,5-Diethyl-3-dichloromethylthiophene 2,5-Diethyl-3-thiophenecarboxaldehyde produced in a) (2.6 g, 15 mmol) in ether (30 ml) was treated with phosphorus pentachloride (3.4 g, 16 mmol) in ether (30 ml) at 20° C. After 30 min, the solution was poured onto ice-water (50 ml) and petroleum (20 ml) was added. Work up as in example 8b) afforded 2,5-diethyl-3-dichloromethylthiophene (2.9 g, 84%) as a clear oil which was pure by n.m.r. (Found M+: 222.0015 $C_9H_{12}SCl_2$ requires M, 222.0037) which showed $\nu_{max}$ (film) 734s, 1202m, 1457m, 1675m, 2932m and 2970s cm$^{-1}$; $\delta_H$(CCl$_4$) 1.28 (6H, t, J 7 Hz), 2.71 (4H, br q. J 7 Hz), 6.51 (1H, s), 6.77 (1H, br s, W$_\frac{1}{2}$ 4 Hz); m/z 222 (M+), 187 (M+-Cl).

c) 1-Chloro-1-(2,5-diethyl-thien-3-yl)-2,2,3,3-tetramethylcyclopropane

In a process similar to that described in example 7, potassium-t-butoxide (0.25 g, 2.2 mmol) was added in one portion to a rapidly stirred solution of 2,5-diethyl-3-dichloromethylthiophene produced in b) (0.23 g, 10.0 mmol) and 2,3-dimethylbut-2-ene (1.0 g, 12 mmol) at 20° C. After 1 h at ambient temperature, water (30 ml) and light petroleum (30 ml) were added. The organic extract was washed with more water, dried, and evaporated to give the crude cyclopropane as a dark oil. Rapid chromatography on silica (eluent: light petroleum-ethyl acetate (5:1)) yielded only one product, identified as 2,4-dimethyl-3-(2,5-diethylthien-3-yl)-penta-1,3-diene (18) (30 mg, 13%) (Found M+ 234.1448. $Cl_{15}H_{22}S$ requires M, 234.1442) which showed $\nu_{max}$ (film) 837w, 894m, 1456m. 1631w, 2929m and 2967s cm$^{-1}$; $\delta_H$(CCl$_4$) 1.2 (6H, m), 1.48 (3H, s), 1.57 (3H, s), 1.77 (3H, s), 2.59 (4H, m), 4.64 (1H. br s, W 6 Hz), 4.81 (1H, br s, W$_\frac{1}{2}$ 6 Hz), 6.12 (1H, s); m/z 234 (M+), 219 (M+-CH$_3$), 205 (M+-C$_2$H$_5$).

EXAMPLE 10 a) 3-Ethyl-2-thiophenecarboxaldehyde

Lithium aluminium hydride (0.3 g, 9.0 mmol) was added in small portions over 10 min to a stirred solution of 3-ethyl-2-cyanothiophene (formed by the electrophilic cyanation of 3-ethylthiophene with chlorosulphonyl isocyanate and dimethyl formamide as described by Gronowitz et al in Acta Chem. Scand. B31 (1977) 771–780) (1.00 g, 7.3 mmol) in ether (30 ml). After 2 h at 20° C. followed by 1 h at 30° C., the mixture was quenched with water (2 ml). Light petroleum (30 ml) was added and the organic extract washed with 10% hydrochloric acid (50 ml) followed by water (30 ml). After drying, the solvent was removed to give an oil which contained several products. This procedure was repeated on a larger scale using 2.22 g (16.2 mmol) of the starting compound. The product mixtures were combined and purified by chromatography on silica, eluting with light petroleum-ethyl acetate (4:1) to provide 3-ethyl-2-thiophenecarboxaldehyde (0.36 g, 11%) as a clear yellow oil (Found M+: 140.0297. $C_7H_8SO$ requires M, 140.0296) which showed $\nu_{max}$ (film) 668m, 1199m, 1243m, 1425m, 1657s, 2873m and 2971m cm$^{-1}$; $\delta_H$(CCl$_4$) 1.27 (3H, t, J 8 Hz), 2.96 (2H, q, J 8 Hz), 6.82 (1H, d, J 5 Hz), 7.40 (1H, d, J 5 Hz), 9.77 (1H, s); m/z 140 (M+), 125 (M+-CH$_3$), 111 (M+-CHO).

b) 3-Ethyl-2-dichloromethylthiophene

3-Ethyl-2-thiophenecarboxaldehyde produced in a) (0.30 g, 2.1 mmol) in ether (15 ml) was added dropwise to a stirred suspension of phosphorus pentachloride (0.53 g, 2.5 mmol) in ether (15 ml) at 20° C. After 15 min at 20° C. no aldehyde remained (n.m.r.). The ether was evaporated and replaced with light petroleum (40 ml). The solution was poured onto ice water (50 ml), the organic phase was separated and quickly washed with ice-cold saturated sodium hydrogen carbonate (20 ml) followed by water. After drying, the solvent was removed and replaced by petroleum. After standing overnight at −10° C., the solution was decanted from the black residue and evaporated to afford 3-ethyl-2-dichloromethylthiophene (0.33 g, 80%) as a clear yellow oil which contained a minor amount (ca. 10%) of the aldehyde (Found M+: 193.9748. $C_7H_8SCl_2$ requires M, 193.9724) which showed $\delta_H$(CCl$_4$) 1.23 (3H, t, J 7 Hz), 2.66 (2H, q, J 7 Hz, 6.72 (1H, d, J 5 Hz) 6.85 (1H, s), 7.18 (1H, d, J 5 Hz); m/z 194 (M+), 159 (M+-Cl).

This material was susceptible to hydrolysis and thermal decomposition and so was used immediately.

c) 1-Chloro-1-(3-ethylthien-2-yl)-2,2,3,3-tetramethylcyclopropane

Potassium-t-butoxide (0.30 g, 2.7 mmol) was added in small portions over 5 min to a stirred solution of crude 3-ethyl-2-dichloromethylthiophene produced in b) (0.14 g, 0.72 mmol) and 2,3-dimethylbut-2-ene (1.0 g, 12 mmol) in ether (10 ml) at 20° C. After 15 min the solution was poured onto water (50 ml), light petroleum (40 ml) was added and the organic extract was washed several times with water. The product was dried and the solvent removed to yield a clear red/brown oil provisionally identified as 1-chloro-1-(3-ethylthien-2-yl)-2,2,2,2-tetramethylcyclopropane (ca. 90 mg, 50%) which showed $\delta_H$ (CCl$_4$) 1.0–1.5 (15H, complex m), 2.55 (2H, q, J 7 Hz), 6.75 (1H, d, J 5 Hz), 7.0 (1H, d, J 5 Hz). Rapid chromatography through a small bed of silica, eluting with hexane, resulted in ring opening and some decomposition. Only one product was eluted and characterised as 2,4-dimethyl-3-(3-ethylthien-2-yl)-penta-1,3-diene (30 mg, 20%) (Found M+: 206.1146 $Cl_3H_{18}S$ requires M, 206.1129) which showed $\nu_{max}$ (film) 899s, 1370m, 1443s, 1632w, 2854s, 2931s, 2966s and 3077w cm$^{-1}$; $\delta_H$(CCl$_4$) 1.13 (3H, t, J 7 Hz), 1.60 (3H, s), 1.68 (3H, s), 1.88 (3H, s), 2.40 (2H, q, J 7 Hz), 4.77 (1H, br s, W$_\frac{1}{2}$ 6 Hz), 4.90 (1H, br s, W 6 Hz), 6.72 (1H, d, J 5 Hz), 6.99 (1H, d, J 5 Hz); m/z 206 (M+), 191 (M+-CH$_3$).

EXAMPLE 11 a) 3-Methyl-2-dichloromethylthiophene

3-Methyl-2-thiophenecarboxaldehyde (3.05 g, 24 mmol) in dry ether (10ml) was added dropwise to a stirred suspension of phosphorus pentachloride (5.0 g, 24 mmol) in dry ether (30 ml) at 0° C. After 10 min at 0° C., the mixture was filtered and the solvent removed to leave a black oil which was taken up in light petroleum (30 ml). After standing for 1 h, the clear liquid was decanted from a black residue and filtered. The process was repeated several times until a clear, pale yellow solution resulted. Removal of the solvent afforded crude 3-methyl-2-dichloromethylthiophene (4.4 g) in almost quantitative yield, as a black oil containing ca.

5% aldehyde (Found M+: 179.9574 $C_6H_6SCl_2$ require M, 179.9566) which showed $\delta_H$(CCl$_4$) 2.26 (3H, s), 6.67 (1H, d, J 5 Hz), 6.84 (1H, s), 7.12 (1H, d, J 5 Hz); m/z 180 (M+), 145 (M+-Cl).

The product polymerises rapidly at room temperature and is extremely susceptible to hydrolysis; it was therefore used immediately without purification.

b) 1-Chloro-1-(3-methylthien-2-yl)-2,2-dimethylcyclopropane

Potassium-t-butoxide (5.0 g, 44 mmol) was added over 10 min to a stirred solution of crude 3-methyl-2-dichloromethylthiophene produced as in a) (4.0 g, 22 mmol) and excess 2-methylpropene (about 10 ml, 7 g, 0.13 mol) in dry ether (40 ml) at 0° C. After 30 min at 0° C. the mixture was diluted with water (10 ml), the ether extract was separated and the ether removed. The residue was taken up in light petroleum (30 ml) and washed with water (3×30 ml). The organic extract was dried and the solvent evaporated to yield the crude cyclopropane as a red/brown oil (2.3 g, 26%) which was free from aldehyde and dichloride. A portion of this product (1.25 g) was distilled at reduced pressure (oven temperature 65° C. at 0.1 mmHg) to afford 1-chloro-1-(3-methylthien-2-yl)-2,2-dimethylcyclopropane (0.75 g, 16%) as a colourless oil which was pure by n.m.r. (Found M+: 200 0421. $C_{10}H_{13}SCl$ requires M, 200.0426) which showed $\delta_H$ (CCl$_4$) 0.92 (3H, s), 1.20 (2H, narrow m), 1.45 (3H, s), 2.20 (3H, s), 6.65 (1H, d, J 5 Hz), 6.90 (1H, d, J 5 Hz); m/z 200 (M+), 185 (M+-CH$_3$), 165 (M+-Cl).

EXAMPLE 12 a)

3-Phenyl-2-thiophenecarboxaldehyde was prepared by Vilsmeier formylation of 3-phenylthiene. Although this reaction is reported to give a 94:6 ratio of 2,3 to 2,4 substituted compounds, the product, after chromatography, appeared to be only one isomer and was identical to an authentic sample of the 2-aldehyde.

b) 3-Phenyl-2-dichloromethylthiophene

3-Phenyl-2-thienecarboxaldehyde produced as in a) (2.24 g, 12 mmol) in ether (20 ml) was added dropwise to a stirred suspension of phosphorus pentachloride (2.6 g, 12.5 mmol) in dry ether (25 ml) at 0° C. The mixture was stirred at 0° C. until the solution became clear (30 min) and then poured onto ice-water (200 ml). After separating the layers, the ether was evaporated and replaced with light petroleum (30 ml). The organic extract was washed with saturated sodium hydrogen carbonate solution (2×50 ml) followed by water, dried, and the solvent evaporated to yield 3-phenyl-2-dichloromethylthiophene (2.40 g, 83%) as an orange syrup. The product was pure by t.l.c. and n.m.r. (Found M+: 241.9711. $C_{11}H_8SCl_2$ requires M, 241.9724) and showed $\nu_{max}$ (film) 700s, 736s, 772s, 1178m and 1489m cm$^{-1}$; $\delta_H$ (CCl$_4$) 6.70 (1H, s), 6.75 (1H, d, J 5 Hz), 7.2 (6H, narrow m); m/z 242 (M+), 207 (M+-Cl).

c) 1-Chloro-1-(3-phenylthien-2-yl)-2,2-dimethylcyclopropane

Potassium-t-butoxide (0.25 g, 2.2 mmol) was added in one portion to a stirred solution containing 3-phenyl-2-dichloromethylthiophene produced in b) (0.25 g, 1.0 mmol) and 2-methylpropene (1.0 g, 18 mmol) in dry ether (10 ml) at 0° C. After 5 min the solution was allowed to attain room temperature and stirred for an additional 30 min. Light petroleum (20 ml) was added, followed by water (50 ml) and the organic phase was separated and washed several times with water. Work up as in example 11b) above and stirring with silica (0.5 g) in CCl$_4$ (10 ml) for 10 min at room temperature followed by filtration and evaporation removed trace impurities to afford 1-chloro-1-3-phenylthien-2-yl)-2,2-dimethylcyclopropane as a clear syrup (2.00 g, 75%) (Found M+: 262.0594. $C_{15}H_{15}SCl$ requires M, 262.0583) which showed $\nu_{max}$ (film) 698s, 728s, 1067m, 1449m, 1490m, 2926m and 2954m cm$^{-1}$; $\delta_H$(CCl$_4$) 0.68 (3H, s), 0.99 (1H, d, J 6 Hz), 1.15 (1H, d, J 6 Hz), 1.35 (3H, s), 6.85 (1H, d, J 6 Hz), 7.0–7.6 (6H, m); m/z 262 (M+), 247 (M+-CH$_3$), 227 (M+-Cl).

EXAMPLE 13

3a) 3-Methoxymethyl-2-thiophenecarboxaldehyde

Reaction of 3-bromomethylthiophene with sodium methoxide in methanol provided 3-methoxymethylthiophene (84%). n-Butyl lithium (30 ml, 1.5 M, 45 mmol) was slowly added to 3-methoxymethylthiophene (5.0 g, 39 mmol) in dry ether (100 ml) at 25° C. After stirring for 1 h, N,N-dimethylformamide (5.7 g, 78 mmol) in dry ether (200 ml) was added dropwise and the resultant solution was stirred for an additional 18 h at 20° C. Water (5 ml) was added and the organic phase washed with 5% hydrochloric acid (100 ml) followed by water (100 ml) and dried. The solvent was removed to yield the crude product (5.2 g, 85%) which was essentially pure by n.m.r. Distillation afforded the title compound (3.80 g, 62%) as a colourless oil, b.p. 73°–75° C. at 0.25 mmHg (Found M+: 156.0256. $C_7H_8O_2S$ requires M, 156.0245) which showed $\nu_{max}$ (film) 667m, 1107m, 1200w, 1426m, 1662s, 2930w and 3100w cm$^{-1}$; $\delta_H$ (CCl$_4$) 3.35 (3H, s), 4.66 (2H, s), 7.05 (1H, d, J 5 Hz), 7.49 (1H, d, J 5 Hz), 9.87 (1H, s); m/z 156 (M+), 141 (M+-CH$_3$).

b) 3-Methoxymethyl-2-dichloromethylthiophene

3-Methoxymethyl-2-thiophenecarboxaldehyde (1.50 g, 9.6 mmol) in dry ether (20 ml) was added over 5 min to a stirred suspension of phosphorus pentachloride (2.5 g, 12 mmol) in ether (20 ml). After 20 min at room temperature no starting material remained and the solution was colourless. The ether was removed and replaced with light petroleum (25 ml). After washing several times with ice-cold water, the organic extrct was dried and the solvent removed to yield 3-methoxymethyl-2-dichloromethylthiophene (1.03 g, 51%) as a dark oil containing a small amount (ca. 10%) of aldehyde. As the product is susceptible to hydrolysis and decomposition, it was identified by $^1$H n.m.r. and used immediately without purification and showed $\delta_H$(CCl$_4$) 3.33 (3H, s), 4.44 (2H, s), 6.73 (1H, d, J 5 Hz), 7.10 (1H, s) 7.17 (1H, d, J 5 Hz).

c) 1-Chloro-1-(3-methoxymethylthien-2-yl)-2,2,3,3-tetramethylcyclopropane

Potassium-t-butoxide (0.35 g, 3.0 mmol) was added over 5 min to a rapidly stirred solution of 2-dichloromethyl-3-methoxymethylthiophene produced as in b) (0.25 g, 1.2 mmol) and 2,3-dimethylbut-2-ene (1.0 g, 12 mmol) in dry ether (15ml) at 20° C. After 30 min, water (30 ml) and light petroleum (30 ml) were added and the organic extract was washed several times with water. After drying, the solvent was removed to give a brown oil which consisted of the cyclopropane as the major product ($^1$H n.m.r.). Rapid chromatography on silica, eluting with light petroleum-ethyl acetate (6:1) afforded the title compound (60 mg, 19%) as a clear oil which was pure by n.m.r. (Found M+: 258.0839. C$_{13}$H$_{19}$SOCl requires M, 258.0845) which showed $\nu_{max}$ (film) 814m, 1104s, 1190m, 1379m, 1450m, 2820m, 2923s and 3006m cm$^{-1}$; $\delta_H$ (CCl$_4$) 1.10 (6H, s), 1.32 (6H, s), 3.27 (3H, s), 4.27 (2H, s), 6.87 (1H, d, J 5 Hz), 7.05 (1H, d, J 5 Hz); m/z 258 (M+), 222 (M+-Cl).

EXAMPLE 14

Thermolysis of 3-chloro-3-(3-pyridyl)diazirine (Compound I', Het'=3-pyridyl, X'-Cl) in the presence of alkenes The diazirine was made made from 3-amidinopyridinium chloride by a process similar to that described in Examples 1 and 2.

a)
1-Chloro-1-(3-pyridyl)-2,2,3,3-tetramethylcyclopropane

A stirred solution of the diazirine (0.80 g, 5.2 mmol) and 2,3-dimethylbut-2-ene (3.0 g, 36 mmol) in tetrachloroethene (5 ml) was heated at reflux for 90 min. during which time the mixture darkened due to the formation of a fine suspension. When cool, light petroleum (30 ml) was added and the mixture filtered to give a clear yellow filtrate. Removal of the solvent yielded a viscous oil (0.6 g) which was chromatographed on silica eluting with light petroleum-ethyl acetate (2:1) to afford the title compound as a yellow crystalline solid (0.35 g, 32%) which had a melting point of 52°-53° C.

Found: M+ 209.0991; C, 68.6; H, 7.6; N, 6.6. C$_{12}$H$_{16}$NCl requires M, 209.0971; C, 68.7, H,, 7.7; N, 6.7%.

$\nu_{max}$ (film) 796m, 867m, 1026s, 1380s, 1452s, 1573m and 2922s cm$^{-1}$ $\delta_H$(CCl$_4$) 1.03 (6H, s), 1.33 (6H, s), 7.05 (1H, dd, J 5,8 Hz), 7.40 (1H, d, J 8 Hz, fine splitting), 8.35 (2H, m).

m/z 209 (M+), 194 (M+-CH$_3$), 174 (M+-Cl).

b) 1-Chloro-1-(3-pyridyl)-2-phenylcyclopropane (Compound IV, R$^5$=Ph, R$^6$=R$^7$=R$^8$=H)

The diazirine (1.0 g, 6.5 mmol) was heated with styrene (5.0 g, 48 mmol) in tetrachloroethene (7 ml) at reflux for 90 min. Work up as described in a) above yielded the crude product as an orange syrup (0.32 g, 21%) with an isomer ratio of syn/anti=1.3. Chromatography on silica eluting with light petroleum-ethyl acetate (4:1) gave two fractions. The first was characterised as the syn isomer of the title compound (0.13 g, 9%).

Found: M+ 229.0677. C$_{14}$H$_{12}$NCl requires M, 229.0658.

$\nu_{max}$ (film) 699s, 778m, 1417m and 3032w cm$^{-1}$. $\delta_H$ (200 MHz; CDCl$_3$) 1.95 (2H, m), 3.00 (1H, dd, J 7.7, 10 Hz), 6.78 (1H, m) 7.05 (5H, m), 7.42 (1H, br d, J 7.9 Hz), 8.5 (2H, br m).

m/z 229 (M+), 194 (M+-Cl).

The second fraction consisted of the anti-isomer (81 mg, 5%)

Found: M+ 229.0680. C$_{14}$H$_{12}$NCl requires M, 229.0658.

$\nu_{max}$ (film) 698s, 803m, 1022w, 1415m, 1571w and 3032w cm$^{-1}$.

$\delta_H$ (200 MHz; CDCl$_3$ 1.95 (2H, m), 2.64 (1H, t, J 8.5 Hz), 6.78 (1H, m), 7.30 (5H, narrow m), 7.80 (1H, d, J 7.9 Hz), 8.25 (1H, br d, J 5 Hz), 8.45 (1H, br s).

m/z 229 (M+), 194 (M+-Cl).

c) Methyl 2-chloro-2-(3-pyridyl)cyclopropanecarboxylate (Compound IV, R$^5$=COOMe, R$^6$=R$^7$=R$^8$=H)

A solution of the diazirine (0.60 g, 3.9 mmol) and methyl acrylate (3.8 g, 44 mmol) in tetrachloroethene (10 ml) was heated at reflux (ca. 100° C.) for 60 min. Work up as described in a) yielded the crude product with an isomer ratio of ca. 1:1. The product was purified by chromatography on silica eluting with light petroleum-ethyl acetate (1:1) as eluent to afford only one fraction, a clear oil characterised as an isomeric mixture (syn/anti=6) of the title compound (38 mg, 5%).

Found: M+ 211.0386 C$_{11}$H$_{10}$NO$_2$Cl requires M, 211.0400.

$\nu_{max}$ (film) 756m, 1208s, 1376m, 1440m, 1734s and 2954w cm$^{-1}$ $\delta_H$ (CCl$_4$; mixture) major isomer: 1.9 (2H, m), 2.50 (1H, dd, J 7, 10 Hz), 3.40 (3H, s), 7.02 (1H, dd, J 6, 10 Hz, fine splitting), 7.49 (1H, dd, J 2, 6 Hz), 8.4 (2H, br m).

minor isomer: 3.72 (3H, s) other signals obscured.

m/z 211 (M+), 176 (M+-Cl).

d) Methyl 1-methyl-2-chloro-2-(3-pyridyl)cyclopropane carboxylate (Compound IV, R$^5$=COOMe, R$^6$=Me, R$^7$=R$^8$=H)

A solution of the diazirine (0.5 g, 3.3 mmol) and methyl methacrylate (3.3 g, 33 mmol) in tetrachloroethene (10 ml) was heated at reflux for 60 min. Work up as in a) above yielded the crude product as a red oil consisting of a mixture of isomers (syn/anti=3). Chromatography on silica, eluting with light petroleum-ethyl acetate (3:1) afforded only a single fraction which showed one spot by t.l.c. and was identified as an isomeric mixture of cyclopropanes (syn/anti=3.7) (0.14 g, 18%).

Found M+ 225.0548 C$_{11}$h$_{12}$NO$_2$Cl requires m, 225.0556.

$\nu_{max}$ (film) 712m, 1161m, 1198m, 1304m, 1450w, 1571w, 1731s and 2951w cm$^{-1}$ $\delta_H$(CCl$_4$; mixture) syn isomer 1.37 (1H, d, J 6.5 Hz), 1.73 (3H, s), 2.41 (1H, d, J 6.5 Hz) 3.27 (3H, s), 7.05 (1H, m), 7.50 (1H, m), 8.3 (2H, m).

anti isomer: 1.08 (3H, s), 1.55 (1H, d, J 6.5 Hz), 2.21 (1H, d, J 6.5 Hz), 3.74 (3H, s), 7.05 (1H, m), 7.50 (1H, m), 8.3 (2H, m).

m/z 225 (M+), 210 (M+-CH$_3$), 190 (M+-Cl), 185 (M+-$^{CH_3}$Cl).

e) 1,2-Dichloro-2-(3-pyridyl)cyclopropanecarbonitrile (Compound IV, R$^5$=CN, R$^6$=Cl, R$^7$=R$^8$=H)

A solution of the diazirine (0.60 g, 4.0 mmol) and α-chloroacrylonitrile (2.9 g, 33 mmol) in tetrachloroethene (10 ml) was heated at reflux for 60 min. Work up yielded a crude isomeric mixture (1:1) of cyclopropanes (0.25 g, 29%) which was chromatographed on silica eluting with light petroleum-ethyl acetate (1:1) to give three fractions. The first was identified as the syn isomer of the title compound (48 mg, 6%), a clear oil.

$\nu_{max}$ (film) 711s, 801m, 1017m, 1139w, 1420s, 2243w and 3092w cm$^{-1}$ $\delta_H$(CCl$_4$) 1.97 (1H, d, J 9 Hz), 2.62 (1H, d, J 9 Hz) 7.2 (1H, br m), 7.65 (1H, br d, J 7 Hz), 8.5 (2H, br m).

m/z 212 (M$^+$), 177 (M$^+$-Cl), 142 (M$^+$-Cl$_2$)

The second fraction was a 1:1 mixture of cyclopropanes (98 mg, 12%) while the third fraction was identified as the anti-isomer (25 mg, 3%), a colourless oil which slowly solidified to a white solid having a melting point of 62°-64° C.

Found: M$^+$ 211.9902 C$_9$H$_6$N$_2$Cl$_2$ requires M, 211.9908

$\nu_{max}$(film) 710s, 1014m, 1420s, 1482m, 1573m, 2247m and 3100br cm$^{-1}$ $\delta_H$(CCl$_4$) 2.30 (1H, d, JAB 8 Hz), 2.40 d, JAB 8 Hz), 7.18 (1H, dd, J 5, 8 Hz), 7.66 (1H, d, J 8 Hz, fine splitting), 8.55 (2H, m).

m/z 211 (M$^+$), 177 (M$^+$-Cl), 142 (M$^+$-Cl ).

EXAMPLE 15

3-Chloro-3-(2-pyridyl)-3H-1,2-diazirine (Compound I', Het'=2-pyridyl, X'=Cl)

2-Amidinopyridinium chloride (12.0 g, 76 mmol) and anhydrous lithium chloride (18 g) were dissolved in DMSO (200 cm$^3$) with stirring at 20° C. A solution containing sodium chloride (80 g) in aqueous sodium hypochlorite (500 cm$^3$, 2M) was added quickly with care to the vigorously stirred amidine solution so the temperature increased rapidly to 55°-60° C.; this was accompanied by a deep red-pink coloration which soon faded to yellow. The mixture was maintained at 40°-50° C. for 30 min and then extracted with light petroleum (3×80 ml). The combined organic extracts were washed with water (2×80 ml), dried, and the solvent was removed to leave the title compound (3.78 g,, 32%) which was pure by n.m.r. and t.l.c. (R$_f$0.8; Petroleum).

$\nu_{max}$(film) 690m, 779s, 935s, 1070m, 1435s, 1467s and 1579s (N=N) cm$^{-1}$ $\delta_H$ (CDCl$_3$) 7.10-7.40 (1H, m), 7.68 (2H, d, J 5 Hz), 8.43 (1H, d, J 5 Hz, fine splitting).

m/z 125 (M$^+$-N ), 118 (M$^+$-Cl).

In another preparation of the diazirine where the yield was only 20% (the reaction temperature did not rise above 50° C.), concentrating and cooling the petroleum extract afforded N-chloro-2-amidinopyridine. These reaction conditions are thus less favourable for producing the desired diazirine.

EXAMPLE 16

Thermolysis of 3-chloro-3-(2-pyridyl)diazirine in the presence of alkenes a) 1,1,2,2,3-Pentachloro-3-(2-pyridyl)cyclopropane (Compound IV, R$^5$=R$^6$=R$^7$R$^8$=Cl)

A solution of the diazirine made in example 15 (0.60 g, 3.9 mmol) in tetrachloroethene (10 ml) was heated at reflux for 90 min. When cool, the mixture was diluted with light petroleum (30 ml) filtered, and solvent removed at reduced opressure to leave a crystalline solid. Recrystalisation from ethanol afforded the title compound as colourless cubic crystals ( 65 mg, 6%) with melting point 132°-134° C.

Found: C, 32.5; H, 1.2; N, 4.6. C$_8$H$_4$NCl$_5$ requires C, 33.0; H, 1.4; N, 4.8%

$\nu_{max}$ (KBr) 695s, 772s, 842s, 1432m, 1464m, 1584m and 3057m cm$^{-1}$ $\delta_H$ (CDCl$_3$) 7.0-7.8 (3H, complex m), 8.50 (1H, m). m/z 254 (M$^+$-Cl), 219 (M$^+$-$^2$Cl).

b) 1-Chloro-1-(2-pyridyl)-2,2,3,3-tetramethylcyclopropane

A stirred solution of the diazirine (0.80 g, 5.2 mmol) and 2,3-dimethylbut-2-ene (3.0 g, 36 mmol) in tetrachloroethene (7 ml) was heated at reflux for 90 min. When cool, the reaction was diluted with light petroleum (20 ml), filtered, and the solvent removed to leave a solid (1.1 g) which consisted of the tetramethylcyclopropane and a second minor product believed to be the pentachlorocyclopropane (n.m.r. and t.l.c.). Chromatography on silica eluting with light petroleum/ethyl acetate (2:1) followed by recrystallisation from light petroleum afforded the title compound as colourless cubic crystals (0.67 g, 62%) having a melting point of 100°-102° C.

Found: C, 68.8; H, 7.6; N, 6.6. C$_{12}$H$_{16}$NCl requires C, 68.7; H, 7.7; N, 6.7%.

$\nu_{max}$ (KBr) 769s, 875s, 1467s, 1583s, 2922s, 2949s and 3001s cm$^{-1}$ $\delta_H$ (CDCl$_3$) 1.06 (6H, s), 1.37 (6H, s), 7.1 (2H, complex m), 7.5 (1H, complex m), 8.48 (1H, d, J 6 Hz, further split)

m/z 194 (M$^+$-CH$_3$), 179 (M$^+$-$^2$CH$_3$), 174 (M$^+$-Cl)

c) 1-Chloro-1-(2-pyridyl)-2-phenylcyclopropane (Compound IV R$^5$=Ph, R$^6$=R$^7$=R$^8$=H)

A stirred solution of the diazirine (0.80 g, 5.2 mmol) and styrene (5.0 g, 48 mmol) in tetrachloroethene (5 ml) was heated at reflux for 90 min. Work up as above yielded the crude product (1.0 g, 84%) with an isomer ratio of syn/anti=1.3 as determined by integration of the α-pyridine protons in the $^1$H n.m.r. spectrum. Chromatography on silica with light petroleum-ethyl acetate (3:1) as eluent afforded two fractions. The first was characterised as the anti isomer of the title compound (0.18 g, 15%).

Found: M$^+$: 228 0670 C$_{14}$H$_{12}$NCl requires M, 229.0658.

$\nu_{max}$ (film) 697s, 1434s, 1465s, 1587s and 3058w cm$^{-1}$ $\delta_H$ (200 MHz; CDCl$_3$) 1.87 (1H, dd, J 5.6, 8.2 Hz), 2.35 (1H, dd, J 5.6, 9.9 Hz), 3.12 (1H, dd, J 8.2, 9.9 Hz), 7.20 (1H, m), 7.25 (5H, m), 7.65 (1H, m), 7.82 (1H, m), 8.50 (1H, m).

m/z 229 (M$^+$), 193 (M$^+$-HCl)

The second fraction consisted of an isomeric mixture (0.68 g, 57%) with syn/anti=2.0; however, repeated chromatography of this fraction afforded a pure sample of the syn isomer of the title compound (28 mg, 2%).

Found: M$^+$ 229.0677 C$_{14}$H$_{12}$NCl requires M, 229.0658.

$\nu_{max}$ (film) 698s, 773s, 1433s, 1470m, 1588m and 3060w cm$^{-1}$ $\delta_H$(200 MHz; CDCl$_3$) 1.90 (1H, dd, 6.6, 10.1 Hz), 2.61 (1H, dd, J 6.6, 8.0 Hz), 3.00 1H, dd, J 8.0, 10.1 Hz), 6.90 (1H, m), 7.0 (5H, m), 7.4 (2H, m), 8.33 (1H, d, J 4 Hz, fine splitting).

m/z 229 (M$^+$), 193 (M$^+$-HCl)

d) Methyl 2-chloro-2-(2-pyridyl)cyclopropanecarboxylate (Compound IV, R$^5$=COOMe, R$^{6\ 8}$=H)

The diazirine (0.5 g, 3.3 mmol) and methyl acrylate (3.8 g, 44 mmol) were heated in tetrachloroethene (8 ml) as described in b) above to give the crude product as an isomeric mixture (syn/anti=1.3). Chromatography on silica eluting with light petroleum-ethyl acetate (2:1) gave two fractions. The first was identified as the anti-isomer of the title compound (0.13 g, 19%).

Found: M+ 211.0409 $C_{10}H_{10}NO_2Cl$ requires M, 211.0400

$\nu_{max}$ (film) 780m, 1171m, 1436m, 1587w, 1740s, 2952w and 3007s and 3007w cm$^{-1}$.

$\delta_H$ (200 MHz; CDCl$_3$) 2.10 (1H, dd, J 5.6, 7.7 Hz), 2.18 (1H, dd, J 5.6, 9.0 Hz), 2.84 (1H, dd, J 7.7, 9.1 Hz), 3.79 (3H, s), 7.18 (1H, dd, J 4.8, 7.55 Hz, fine splitting), 7.71 (1H, dt, J 1.8, 7.8 Hz), 7.88 (1H, d, J 7.8 Hz, further split), 8.46 (1H, d, J 4.8 Hz, further split).

m/z 211 (M+), 196 (M+-CH$_3$), 176 (M+-Cl)

The second fraction, a clear yellow oil was characterised as the syn-isomer of the title compound.

Found: M+ 211.0417 $C_{10}H_{10}NO_2Cl$ requires M, 211.0400.

$\nu_{max}$ (film) 769m, 1163m, 1208m, 1375m, 1438m, 1588w, 1735s, 2952w and 3009w cm$^{-1}$ $\delta_H$ (200 MHz; CDCl$_3$) 1.90 (1H, dd, J 6.4, 9.3 Hz), 2.31 (1H, dd, J 6.4, 7.0 Hz), 2.66 (1H, dd, J 7.0, 9.3 Hz), 3.51 (3H, s), 7.22 (1H, dd, J 4.8, 7.5 Hz, further split), 7.50 (1H, d, J 7.8 Hz, further split), 7.70 (1H, dt, J 1.8, 7.8 Hz), 8.56 (1H, d, J 4.8 Hz, fine splitting).

m/z 211 (M+), 196 (M+-CH$_3$), 176 (M+-Cl).

e) Methyl 1-methyl-2-chloro-2-(2-pyridyl)cyclopropanecarboxylate (Compound IV, $R^5$=COOMe, $R^6$=Me, $R^7$=$R^8$=H)

The diazirine (0.50 g, 3.3 mmol) was heated with methyl methacrylate (4.0 g, 40 mmol) in tetrachloroethene (7 ml) at reflux for 60 min. Work up as described afforded the crude product (0.6 g) with an isomer ratio of syn/anti=2.0. Chromatrography on silica, eluting with light petroleum-ethyl acetate (3:1) yielded two fractions. The first was characterised as the anti-isomer of the title compound (0.14 g, 14%).

Found: M+ 225.0559 $C_{11}H_{12}NO_2Cl$ requires M, 225.0556.

$\nu_{max}$ (film) 1157s, 1280m, 1435m, 1588w, 1735s and 2952w cm$^{-1}$.

$\delta_H$ (CCl$_4$) 0.93 (3H, s), 2.00 (1H, d, J 6 Hz), 2.22 (1H, d, J 6 Hz), 3.62 (3H, s), 6.95 (1H, m), 7.55 (2H, m), 8.25 (1H, d, J 4 Hz, fine splitting).

m/z 225 (M+), 210 (M+-CH$_3$), 189 (M+-HCl & CH$_3$).

The second fraction was characterised as the syn isomer (0.36 g, 48%)

Found: M+ 225.0550 C11H22NO2Cl requires M, 225.0556.

$\nu_{max}$ (film) 777w, 1161m, 1305m, 1435m, 1588w, 1730s, 2950w and 3000w cm$^{-1}$.

$\delta_H$(CCl$_4$) 1.33 (1H, d, J 6 Hz), 1.70 (3H, s), 2.54 (1H, d, J 6 Hz), 3.25 (3H, s), 6.95 (1H, m), 7.35 (2H, m), 8.25 (1H, d, J 4 Hz, fine splitting).

m/z 225 (M+), 210 (M+-CH$_3$), 189 (M+-HCl).

f) 1,2-Dichloro-2-)2-pyridyl)cyclopropanecarbonitrile (Compound IV, $R^5$=CN, $R^6$=Cl, $R^7$=$R^8$H)

The diazirine (0.6 g, 3.9 mmol) and α-chloroacrylonitrile (2.9 g, 33 mmol) were heated in tetrachloroethene (8 ml) to yield the crude cyclopropane (0.8 g) with an isomer ratio of 3:2 in favour of the syn isomer. Chromatography on silica eluting with light petroleum-ethyl acetate (3:1) was accompanied by some decomposition as evident by the purple colouration of the column. Three fractions were eluted; the first was identified as the syn isomer of the title compound (0.21 g, 25%).

$\nu_{max}$ (film) 783s, 1435s, 1466s, 1586s, 2244w and 3099s cm$^{-1}$ $\delta_H$ (CCl$_4$) 1.91 (1H, d, J 8 Hz), 3.37 (1H, d, J 8 Hz), 7.15 (1H, m), 7.65 (2H, m), 8.35 (1H, m).

$\delta_C$ (50 MHz; CDCl$_3$) 30.54 (t), 35.46 (s), (53.11 (s), 115.23 (s), 123.61 (d), 124.07 (d), 137.46 (d), 148.83 (d), 152.86 (s).

m/z 212 (M+), 185 (M+-HCN), 177 (M+-HCl)

This fraction was contaminated by a trace amount of the pentachlorocyclopropane detected in the mass spectrum at 254 (M+-HCl) and in the $^{13}C$ spectrum at $\delta_C$ 122.69, 123.51, 136.99, 149.18 and so a mass measurement was not obtained. The second fraction consisted of a mixture of isomers (anti/syn=1.2) (0.26 g, 32%), while the third fraction was identified as the anti-isomer (65 mg, 8%).

Found: M+211.9913 $C_9H_6N_2C_{12}$ requires M, 211.9908.

$\nu_{max}$ (film) 679s, 781m, 975m, 1435s, 1468s, 1588s, 2245m, 3011w and 3099w cm$^{-1}$ $\delta_H$ (CCl$_4$) 2.25 (1H, d, J 8 Hz), 3.08 (1H, d, J 8 Hz), 7.15 (1H, m), 7.63 (2H, narrow m), 8.39 (1H, d, J 5 Hz, further split).

$\delta_C$ (50 MHz; CDCl$_3$) 30.06 (t), 35.71 (s), 50.96 (s), 115.80 (s), 124.36 (d), 125.17 (d), 137.35 (d), 148.74 (d), 152.29 (s).

m/z 212 (M+), 185 (M+-HCN), 177 (M+-HCl)

g) Methyl 2-chloro-2-(2-pyridyl)-3,3-dimethylcyclopropane carboxylate (Compound I, $R^5$=COOMe, $R^6$=H, $R^7$=$R^8$=Me)

A solution of the diazirine (0.50 g, 3.3 mmol) and methyl 3,3-dimethylacrylate (2.4 g, 21 mmol) in tetrachloroethene (5 ml) was heated at reflux for 60 min. Work up as before yielded the crude product as an isomeric mixture of cyclopropanes (syn/anti=1.7). Chromatography on silica, eluting with light petroleum-ethyl acetate (3:1) provided three fractions. The first, a white crystalline solid was identified as the pentachlorocyclopropane (15 mg, 2%). The second fraction, a clear oil was identified as the anti-isomer of the title compound (0.13 g, 16%).

$\nu_{max}$ (film) 1111m, 1165m, 1225m, 1435s, 1588m, 1741s and 2954m cm$^{-1}$.

$\delta_H$ (CCl$_4$) 0.86 (3H, s), 1.55 (3H, s), 3.00 (1H, s), 3.63 (3H, s), 7.05 (1H, m), 7.55 (2H, br d, J 4 Hz, fine splitting).

m/z 239 (M+, 224 (M+-CH$_3$), 204 (M+-Cl), 180 (M+-CO$_2$CH$_3$)

The third fraction to be eluted was identified as the syn-isomer (0.20 g, 25%).

$\nu_{max}$ (film) 772s, 1116w, 1165s, 1436m, 1587m, 1738s, 2931w and 2953w cm$^{-1}$ $\delta_H$ (CCl$_4$) 1.25 (3H, s), 1.59 (3H, s), 2.10 (1H, s), 3.57 (3H, s), 7.10 (2H, m), 7.5 (1H, m), 8.38 (1H, br d, J 4 Hz).

m/z 204 (M+-Cl), 180 (M+-CO$_2$CH$_3$).

We claim:

1. A compound of the formula I:

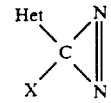

in which Het represents a 5- or 6-membered aromatic ring containing one or two hetero atoms selected from the group consisting of oxygen, sulphur and nitrogen with the proviso that at least one heteroatom is oxygen or sulphur and is attached via a ring carbon atom and X is halogen, alkyl, alkaryl, cyano, alkoxy, or mono- or di-alkylamino.

2. A compound according to claim 1 in which X is a halogen atom.

3. A compound according to claim 1 in which Het is a 2- or 3-thienyl or -furyl group.

4. A compound according to claim 2 wherein X is bromine.

5. A compound according to claim 2 wherein X is chlorine.

6. A compound according to claim 2 wherein Het is a thienyl group.

* * * * *